United States Patent [19]

Specht et al.

[11] 4,147,552

[45] Apr. 3, 1979

[54] LIGHT-SENSITIVE COMPOSITIONS WITH 3-SUBSTITUTED COUMARIN COMPOUNDS AS SPECTRAL SENSITIZERS

[75] Inventors: Donald P. Specht, Spencerport; Samir Y. Farid, Rochester, both of N.Y.

[73] Assignee: Eastman Kodak Company, Rochester, N.Y.

[21] Appl. No.: 769,621

[22] Filed: Feb. 17, 1977

Related U.S. Application Data

[63] Continuation-in-part of Ser. No. 688,664, May 21, 1976, abandoned, which is a continuation-in-part of Ser. No. 654,485, Feb. 2, 1976, abandoned.

[51] Int. Cl.$^2$ .................... G03C 1/70; G03C 1/68; G03C 1/71
[52] U.S. Cl. .................... 96/115 R; 96/35.1; 96/48 HD; 96/49; 96/75.86 P; 96/91 N; 96/115 P; 96/139; 96/140
[58] Field of Search ............... 96/91 N, 91 R, 115 R, 96/115 P, 75.86 P, 84 UV, 139, 140, 90 R, 90 PC, 86 P

[56] References Cited

U.S. PATENT DOCUMENTS

| | | | |
|---|---|---|---|
| 1,965,710 | 7/1934 | Murray | 96/115 R |
| 2,378,583 | 6/1945 | Schmidt et al. | 96/91 R |
| 2,610,120 | 9/1952 | Minsk et al. | 96/115 R |
| 2,670,285 | 2/1954 | Minsk et al. | 96/35.1 |
| 2,670,286 | 2/1954 | Minsk et al. | 96/35.1 |
| 2,670,287 | 2/1954 | Minsk et al. | 96/115 R |
| 2,690,966 | 10/1954 | Minsk et al. | 96/115 R |
| 2,732,301 | 1/1950 | Robertson et al. | 96/115 R |
| 3,030,208 | 4/1962 | Schellenberg et al. | 96/35.1 |
| 3,260,599 | 7/1966 | Lokken | 96/75 |
| 3,525,618 | 8/1970 | Keller | 96/75 |
| 3,533,797 | 10/1970 | Hockessin et al. | 96/90 R |
| 3,546,180 | 12/1970 | Caldwell et al. | 528/290 |
| 3,567,453 | 3/1971 | Borden | 96/91 R |
| 3,620,732 | 11/1971 | Steppan | 96/33 |
| 3,632,344 | 1/1972 | Moraw | 96/84 UV |
| 3,661,591 | 5/1972 | Reed | 96/75 |
| 3,756,827 | 9/1973 | Chang | 96/86 P |
| 3,778,274 | 12/1973 | Inoue et al. | 96/49 |
| 3,779,989 | 12/1973 | Wadsworth et al. | 260/900 |
| 3,782,938 | 1/1974 | DeBoer | 96/35.1 |
| 3,791,845 | 2/1974 | Tuite | 96/84 UV |
| 3,796,727 | 3/1974 | Deboer | 260/345.2 |
| 3,854,950 | 12/1974 | Held | 96/84 UV |
| 3,904,420 | 9/1975 | Hunter | 96/84 UV |
| 3,929,489 | 12/1975 | Arcesi et al. | 96/115 R |

FOREIGN PATENT DOCUMENTS

| | | | |
|---|---|---|---|
| 1053276 | 12/1966 | United Kingdom | 96/91 R |
| 1310936 | 3/1973 | United Kingdom | 96/115 P |
| 1340698 | 12/1973 | United Kingdom | 96/115 R |

OTHER PUBLICATIONS

Wells, C.H.J., "Introduction to Molecular Photochemistry", pp. 59, 60 and 72.
Delzenne, G.A., *J. Macromol. Sci., Rev. Polym. Technol.*, 1971, 1 (2), pp. 185, 196 and 197.
*Research Disclosure*, vol. 152, Public No. 15224, 12/1976, pp. 28-31.
Borden, D., "Review of Light-Sensitive Tetraarylborates", J. P58E, vol. 16, No. 4, 7/1972, pp. 300-312.
Sethna et al., *Chemical Reviews*, 361, (1945).
Pandya, R. K. et al., *Agr. Univ. Research*, 4, 345 (1955). C.A. 52, 7307b.
Woods, L. L. et al., *J. Chem. Eng. Data*, 12, 624, (1967).
Weidel et al., Monatshaft J. Chemie. 18, p. 347, (1897).
Ven Kataraman, K., "The Chemistry of Synthetic Dyes", vol. V, 1971, pp. 590-608.
Robertson, E. M., "Photosensitive Polymer II", *J. of Applied Photographic Science*, vol. II, Issue No. 6, pp. 308-311, 1959.

*Primary Examiner*—Charles L. Bowers, Jr.
*Attorney, Agent, or Firm*—Dana M. Schmidt

[57] ABSTRACT

3-Substituted coumarins are efficient sensitizers for light-sensitive unsaturated materials such as unsaturated vesiculators which release a gas upon exposure to radiation, unsaturated monomers and photocrosslinkable unsaturated polymers, and azides such as photocrosslinkable polymeric azides used in photomechanical resists and lithographic plates. Water soluble derivatives can be used for aqueous coatable or aqueous processable systems.

24 Claims, No Drawings

LIGHT-SENSITIVE COMPOSITIONS WITH 3-SUBSTITUTED COUMARIN COMPOUNDS AS SPECTRAL SENSITIZERS

This application is a continuation-in-part of U.S. Pat. application Ser. No. 688,664 filed on May 21, 1976, now abandoned, which in turn is a continuation-in-part application of U.S. Pat. application Ser. No. 654,485 filed Feb. 2, 1976, now abandoned.

This invention relates to the photosensitization of light-sensitive materials and particularly to the photosensitization of light-sensitive unsaturated materials such as unsaturated vesiculators which release a gas upon exposure to radiation, unsaturated monomers and photocrosslinkable unsaturated polymers, and azides such as photocrosslinkable polymeric azides used in photomechanical resists and lithographic plates.

It is known in the photographic art to reproduce images by processes which involve imagewise exposure of a radiation-sensitive material to modify the physical characteristics of the material in the areas of the layer which have been exposed. Among the radiation-sensitive materials which have been used in such processes are photohardenable materials such as polymers which are insolubilized or hardened on exposure to actinic radaition. The resulting difference in physical properties between exposed and unexposed areas can be employed to prepare images by such procedures as application of mechanical pressure, application of heat, treatment with solvents, and the like. Thus, the layer can be treated with a solvent for the unhardened material which is a non-solvent for the hardened polymer, thereby removing unhardened material leaving an image of hardened polymer.

It is also known that certain coumarins will function as fluorescent brighteners. However, fluorescence and triplet-excitation are known competing processes such that a substance which fluoresces generally will not produce significant triplet-triplet excitation. It is the triplet-excited state, which, if the energetic requirements are met, leads to the sensitization of a light-sensitive material. Therefore, coumarins known to be good fluorescent brighteners are not known to be good sensitizers for light-sensitive materials.

Alternatively the layer can be heated to a temperature which is between the tackifying point of the material in unexposed areas of the layer and material in exposed areas of the layer so that the lower melting material can be toned with a colored powder or transferred to a receiving surface. Such processes have been employed to prepare lithographic printing plates, stencils, photoresists, and similar photographic and photomechanical images. However, the speed of photopolymerizable materials has been relatively slow and it has been desirable to increase the light insolubilization reaction. As a result, many compounds have been proposed in the past as sensitizers. For example, 2-benzoylmethylene-1-methyl-β-naphthothiazoline (BNTZ), disclosed in U.S. Pat. No. 2,732,301 issued Jan. 24, 1956, is useful as a sensitizer for contact printing materials.

The preparation of BNTZ requires an involved synthesis. Thus new sensitizers have been sought that have speeds comparable to or better than BNTZ, a wider range of spectral response, and an easier synthesis.

We have now discovered new sensitizers for photosensitive materials, including unsaturated monomers, unsaturated polymers, vesiculators, and azides.

SUMMARY OF THE INVENTION

According to one aspect of the invention, there is provided a light-sensitive composition comprising, in admixture, a light-sensitive material selected from simple compounds having nonaromatic unsaturation and polymers containing in the backbone or in pendant groups, moieties that have nonaromatic unsaturation; and a sensitizer having an absorptive maximum between about 250 and about 550 nm and the formula

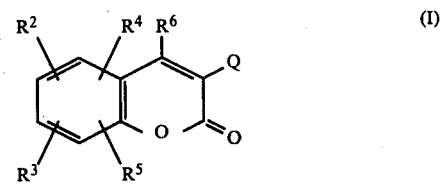
(I)

wherein Q is $-CN$, or $-Z-R^1$; Z is carbonyl, sulfonyl, sulfinyl or arylenedicarbonyl;

$R^1$ is alkenyl; alkyl having 1-12 carbon atoms; aryl of 6-10 nuclear carbon atoms; a carbocyclic group of 5-12 carbon atoms; or a heterocyclic group having 5-15 nuclear carbon and hetero atoms;

$R^2$, $R^3$, $R^4$ and $R^5$ each independently is hydrogen, alkoxy having 1-6 carbon atoms; dialkylamino with each alkyl of the dialkylamino group having 1-4 carbon atoms, halogen, acyloxy, nitro, a 5- or 6-membered heterocyclic group, or a group having the formula

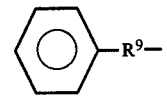

wherein $R^9$ is an alkylene having from 1-5 carbon atoms;

$R^6$ is hydrogen, alkyl having 1-4 carbon atoms, aryl of 6-10 carbon atoms;

and wherein two or three of $R^2$-$R^5$ and the nuclear carbn atoms to which they are attached can together form a fused ring or fused ring system, each ring being a 5- or 6-membered ring;

said sensitizer being present in an amount sufficient to appreciably increase the speed of the composition beyond that which exists without any sensitizer.

A highly useful form of the heterocyclic group for $R^1$ is one selected from the group

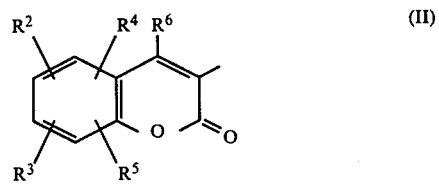
(II)

and a pyridinium group selected from

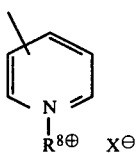

(III)

wherein $R^2$, $R^3$, $R^4$, $R^5$ and $R^6$ are as defined above and $X^\ominus$ is an anion; and $R^8$ is alkyl having 1-4 carbon atoms.

In accordance with another aspect of the invention, there is provided a light-sensitive composition comprising, in admixture, a light-sensitive material selected from simple compounds having nonaromatic unsaturation and polymers containing in the backbone or in pendant groups, moieties that have nonaromatic unsaturation;

and a coumarin having an absorptive maximum between about 250 and about 550 nm and a substituent in the 3-position; the coumarin being present in an amount sufficient to appreciably increase the speed of the composition beyond that which exists without any sensitizer. Highly preferred coumarins are those wherein the 3-substituent is selected from the group consisting of substituted carbonyl, substituted sulfonyl, substituted sulfinyl, cyano, the substituents of the substituted radicals being an organic radical.

In accordance with still another aspect of the invention, the above-noted coumarins can be used in sensitizing amounts with a polymer containing an azide moiety in a side chain attached to the main chain of the polymer. Highly useful forms of such polymers include those wherein said polymer contains a repeating unit with the structure

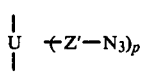

(IV)

wherein U is a recurring unit of the main chain, Z' is selected from the group consisting of alkylene containing 1-5 carbon atoms, carbonyl, aryleneoxy and arylene containing 6-10 carbon atoms, and p is 1 or 2.

In a particularly useful embodiment a coumarin sensitizer of our invention is used with a light-sensitive photopolymerizable material on a suitable support to provide a lithographic plate.

DETAILED DESCRIPTION OF THE INVENTION

The new class of sensitizers for the hereindescribed photopolymerizable materials are coumarins which have an absorptive maximum between about 250 to about 550 nm. As used throughout this specification, "alkenyl", "alkyl" "alkoxy", "aryl", "aryloxy", "carbocyclic", "heterocyclic", "alkoxycarbonyl", "dialkyl amino", "alkylene", "arylene", "aryleneoxy", and the like mean unsubstituted or substituted alkenyl, alkyl, alkoxy, aryl, aryloxy, carbocyclic, heterocyclic, alkoxycarbonyl, dialkyl amino, alkylene, arylene, aryleneoxy, respectively, wherein the substituents, if any, can be any radical which does not destroy the sensitizing effect. For example, such suitable substituents for substituted aryl or aryloxy for $R^1$ of Q of formula (I) above include nitro; alkoxy of 1-5 carbon atom, such as methoxy, ethoxy, and the like; halogen; alkyl and substituted alkyl of 1-5 carbon atoms such as haloalkyl and the like; aryl of 6-10 carbon atoms such as phenyl and the like; carboxy; aryloxycarbonyl of 6-10 nuclear carbon atoms; alkyloxycarbonyl of 2-6 carbon atoms; hydroxy; amino and substituted amino such as dialkylamino and trialkylammonium salt of 1-5 carbon atoms in each alkyl group; acyloxy such as acetoxy, benzoyloxy, substituted benzoyloxy, and the like; acyl such as acetyl, benzoyl and the like; cyano; amido such as acetamido, benzamido and the like; sulfonyl such as methylsulfonyl, fluorosulfonyl, phenylsulfonyl and the like; and sulfo and sulfo salts.

The coumarins of the invention are 3-substituted coumarins. Those that are particularly useful have in the 3-position a substituted carbonyl, substituted sulfonyl, substituted sulfinyl, substituted oxycarbonyl, carboxyl or cyano. Such substituted carbonyls, for example, depending on the light source used, tend as a class to give speed that is comparable, e.g., about ¼ or better, to that of the same composition exposed to the same light source but containing BNTZ sensitizer instead.

Such coumarins can also be described as having the formula:

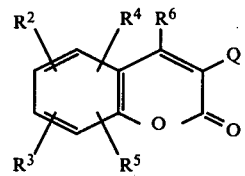

wherein Q is —CN, carboxyl, ammonium or alkali metal salts of carboxyl, or —Z—$R^1$; Z is a linking group selected from carbonyl, sulfonyl, sulfinyl or arylenedicarbonyl;

$R^1$ is hydroxy;

alkenyl, alkyl or alkoxy having 1-12 carbon atoms for example, vinyl, styryl and substituted styryl; methyl, ethyl, propyl, isopropyl, tert-butyl, isobutyl, butyl, amyl, hexyl, heptyl, octyl, nonyl, decyl, including cycloalkyl such as cyclopentyl, cyclohexyl, etc.; methoxy, ethoxy, butoxy, etc.; and including substituted alkenyl and alkyl having a hetero atom in or appended thereto, e.g., oxa, oxo, pyridinium, benzothiazolium, etc.;

aryl of 6-10 nuclear carbon atoms, such as phenyl, naphthyl and the like;

aryloxy such as phenoxy, etc.;

a carbocyclic group such as 1-adamantyl, cyclohexyl and the like;

a heterocyclic group having about 5-15 nuclear carbon and hetero atoms, with or without substituents such as 3-pyridyl, 4-pyridyl, furyl, 2-benzofuranyl, 2-thiazolyl, 2-thienyl, pyridinium having the formula:

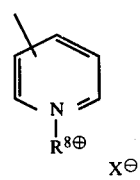

in which $R^8$ is alkyl having 1–4 carbon atoms including methyl, ethyl, propyl, isopropyl, butyl, n-butyl, isobutyl, sec.-butyl, etc., and $X^\ominus$ is an anion including $FSO_3^\ominus$, $BF_4^\ominus$, toluene sulfonate, halogen, e.g., Cl, Br, I, etc.; or a 3-coumarinyl having the formula:

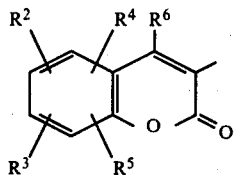

and wherein $R^2$, $R^3$, $R^4$ and $R^5$ are each independently hydrogen; hydroxy; alkoxy having 1–6 carbon atoms, such as methoxy, ethoxy, n-propoxy, iso-propoxy, n-butoxy, pentoxy, and the like; acyloxy, e.g., acetoxy, benzoyloxy and the like; alkoxycarbonyl or 2–6 carbon atoms, e.g., methoxycarbonyl, ethoxycarbonyl and the like; dialkylamino with each alkyl containing 1 to 4 carbon atoms, for example dimethylamino, diethylamino and the like; halogen, for example, chloro, bromo, iodo, and the like; nitro; a 5- or 6-membered heterocyclic group, for example pyrrolidino, morpholino, piperidino, pyridinium, and the like; a halo-substituted alkoxy group, for example β-chloroethoxy, β-iodoethoxy and the like; or a group having the structure

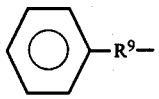

wherein $R^9$ is an alkylene having 1–5 carbon atoms, e.g., methylene, ethylene, etc.; and $R^6$ is hydrogen; alkyl of 1–4 carbon atoms, for example, methyl, ethyl, propyl, isopropyl, and the like; aryl of 6–10 carbon atoms, for example, phenyl, naphthyl and the like; or acyl, for example, acetyl, benzoyl and the like. Some examples or substituents for the substituted alkoxy of $R^2$–$R^5$, which do not destroy the sensitizing effect, include for example, halogens, for example chloro, iodo and the like; sulfo salts; ammonio salt, for example, trimethylammonio salt and the like; hydroxy; acyl, for example acetyl, benzoyl, and the like; and aryl, for example, phenyl, naphthyl, and the like.

Of the foregoing, of particular usefulness are the coumarins having propoxy substituents in the 5 and/or 7 positions, as they provide enhanced solubility which is important in those coating machines that are normally operated at higher concentrations of materials.

It has also been discovered that the coumarins of this invention can be used in admixture with other coumarins or other known sensitizers to provide sensitization, and to provide a greater range of spectral response.

In addition to the aforedescribed coumarins, it is contemplated that coumarins of the following structure are the full equivalents of those heretofore discussed, and will function in the same manner to sensitize light-sensitive materials:

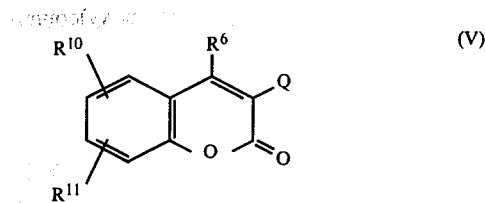

wherein $R^6$ and Q are as defined above and at least one of $R^{10}$ and $R^{11}$ is alkylthio having from 1–10 carbon atoms, for example, methylthio, ethylthio and the like; substituted alkylthio of 1–10 carbon atoms having any substituent appended to the alkyl and useful as for the substituted alkoxy radicals described above; or arylthio having from 6–10 carbon atoms; the other of $R^{10}$ and $R^{11}$ being the same or being selected from those defined for $R^2$ through $R^5$.

Typical coumarins which are useful in our invention include, for example:
3-benzoyl-5,7-dimethoxycoumarin
3-benzoyl-7-methoxycoumarin
3-benzoyl-6-methoxycoumarin
3-benzoyl-8-ethoxycoumarin
7-methoxy-3-(p-nitrobenzoyl)coumarin
3-benzoylcoumarin
3-(p-nitrobenzoyl)coumarin
3-benzoylbenzo[f]coumarin
3,3'-carbonylbis(7-methoxycoumarin)
3-acetyl-7-methoxycoumarin
3-benzoyl-6-bromocoumarin
3,3'-carbonylbiscoumarin
3-benzoyl-7-dimethylaminocoumarin
3,3'-carbonylbis(7-diethylaminocoumarin)
3-carboxycoumarin
3-carboxy-7-methoxycoumarin
3-methoxycarbonyl-6-methoxycoumarin
3-ethoxycarbonyl-6-methoxycoumarin
3-ethoxycarbonyl-7-methoxycoumarin
3-methoxycarbonyl-7-methoxycoumarin
3-acetylbenzo[f]coumarin
3-acetyl-7-methoxycoumarin
3-(1-admantoy)-7-methoxycoumarin
3-benzoyl-7-hydroxycoumarin
3-benzoyl-6-nitrocoumarin
3-benzoyl-7-acetoxycoumarin
3-[3-(p-ethoxyphenyl)acryloyl]-7-methoxycoumarin
3-benzoyl-7-diethylaminocoumarin
7-dimethylamino-3-(4-iodobenzoyl)coumarin
7-diethylamino-3-(4-iodobenzoyl)coumarin
3,3'-carbonylbis(5,7-diethoxycoumarin)
3-(2-benzofuroyl)-7-(1-pyrrolidinyl)coumarin
7-diethylamino-3-(4-dimethylaminobenzoyl)coumarin
7-methoxy-3-(4-methoxybenzoyl)coumarin
3-(4-nitrobenzoyl)benzo[f]coumarin
3-(4-ethoxycinnamoyl)-7-methoxycoumarin
3-(4-dimethylaminocinnamoyl)coumarin
3-(4-diphenylaminocinnamoyl)coumarin
3-[(3-methylbenzothiazl-2-ylidene)acetyl]coumarin
3-[(1-methylnaphtho[1,2-d]thiazol-2-ylidene)acetyl]coumarin
3,3'-carbonylbis(6-methoxycoumarin)
3,3'-carbonylbis(7-acetoxycoumarin)
3,3'-carbonylbis(7-dimethylaminocoumarin)
3,3'-carbonylbis(5,7-di-isopropoxycoumarin)
3,3'-carbonylbis(5,7di-n-propoxycoumarin)
3,3'-carbonylbis(5,7-di-n-butoxycoumarin)
3,3'-carbonylbis[5,7-di(2-phenylethoxy)coumarin]

3,3'-carbonylbis[5,7-di(2-chloroethoxy)coumarin]
3-cyano-6-methoxycoumarin
3-cyano-7-methoxycoumarin
7-methoxy-3-phenylsulfonylcoumarin
7-methoxy-3-phenylsulfinylcoumarin
1,4-bis(7-diethylamino-3-coumarylcarbonyl)benzene
7-diethylamino-5',7'-dimethoxy-3,3'-carbonylbiscoumarin
7-dimethylamino-3-thenoyl coumarin
7-diethylamino-3-furoyl coumarin
7-diethylamino-3-thenoyl coumarin
3-benzoyl-7-(1-pyrrolidinyl)coumarin
3-(4-fluorosulfonyl)benzoyl-7-methoxycoumarin
3-(3-fluorosulfonyl)benzoyl-7-methoxycoumarin
5,7,6'-trimethoxy-3,3'-carbonylbiscoumarin
5,7,7'-trimethoxy-3,3'-carbonylbiscoumarin
7-diethylamino-6'-methoxy-3,3'-carbonylbiscoumarin
3-nicotinoyl-7-methoxycoumarin
3-(2-benzofuroyl)-7-methoxycoumarin
3-(7-methoxy-3-coumarinoyl)-1-methylpyridinium fluorosulfate
3-(5,7-diethoxy-3-coumarinoyl)-1-methylpyridinium fluoroborate
N-(7-methoxy-3-coumarinoylmethyl)pyridinium bromide
3-(2-benzofuroyl)-7-diethylaminocoumarin
7-(1-pyrrolidinyl)-3-thenoylcoumarin
7-methoxy-3-(4-pyridinoyl)coumarin
3,6-dibenzoylcoumarin
N-(7-methoxy-3-coumarinoylmethyl)-N-phenylacetamide
and
9-(7-diethylamino-3-coumarinoyl)-1,2,4,5-tetrahydro3H,6H,10H[1]benzopyrano[9,9a,1-gh]quinolazine-10-one
which has the structure:

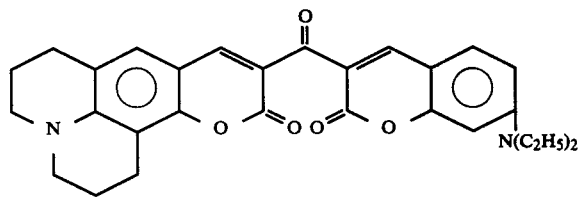

Preparations of organocarbonyl coumarins are found in *Chemical Reviews*, 36 1, (1945), S. M. Sethna and N. H. Shah; R. K. Pandya and K. C. Pandya *Agr. Univ. J. Research* 4, 345 (1955) C. A. 52, 7307b. Bis compounds are described in L. L. Woods and M. Fooladi *J. Chem. Eng. Data* 12, 624 (1967).

Illustrative preparations are as follows:

PREPARATION 1

Preparation of 3-benzoyl-5,7-dimethoxycoumarin.

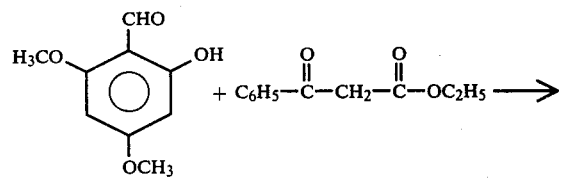

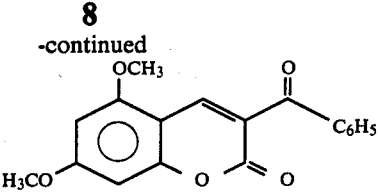

A mixture of 18.2 g 4,6-dimethoxysalicylaldehyde, 20.0 g ethyl benzoylacetate, 20 ml acetonitrile and 30 drops piperidine was heated gently on a hot plate for 45 minutes. After cooling the product was collected and recrystallized twice from acetonitrile and once from benzene containing a small amount of acetonitrile. m.p. 178° C.–179° C.

Analysis: Calc.: C, 69.7; H, 4.5 Found: C, 69.7; H, 4.5

PREPARATION 2

Preparation of 3-acetyl-7-methoxycoumarin.

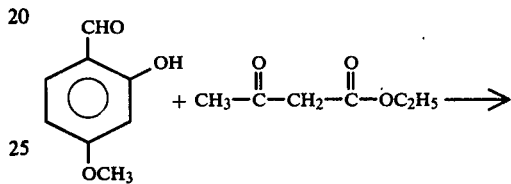

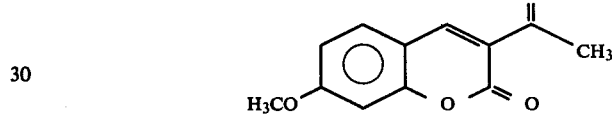

A mixture of 15.2 g 2-hydroxy-4-methoxybenzaldehyde and 13.5 g ethyl acetoacetate was warmed on a hot plate until solution was attained. Thirty drops of piperidine were added and the reaction mixture continued to be heated gently. After several minutes the reaction mixture solidified. After cooling, the product was recrystallized from a mixture of alcohol and acetonitrile. Yield 20 g.

Analysis: Calc.: C, 66.1; H, 4.6 Found: C, 65.7; H, 4.7

PREPARATION 3

Preparation of 3-(4-ethoxycinnamoyl)-7-methoxycoumarin.

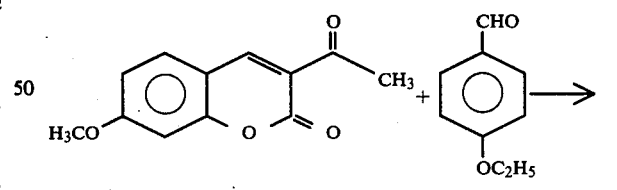

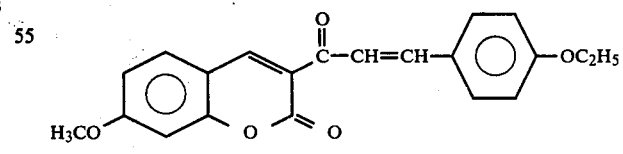

A suspension of 2.18 g 3-acetyl-7-methoxycoumarin and 1.65 g p-ethoxybenzaldehyde in 100 ml alcohol was heated under reflux on a steam bath. Acetonitrile was added until solution was attained. Fifty drops of piperidine were added and the reaction mixture heated under reflux for 90 minutes. An additional fifty drops of piperidine were added and the solution was heated under reflux another hour. The product separated upon cooling and was washed with alcohol before being recrystallized from a mixture of alcohol and acetonitrile.

Analysis: Calc.: C, 72.0; H, 5.2 Found: C, 71.6; H, 5.4

PREPARATION 4

Preparation of 3,3'-carbonylbis(7-diethylaminocoumarin).

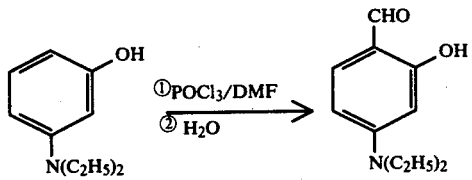

4-diethylaminosalicylaldehyde

① Phosphoryl chloride (61.2 g, 0.40 mole) is added dropwise with stirring and cooling to 90 g dimethylformamide. The temperature is maintained at 25° C. by means of an ice bath as 60.4 g (0.36 mole) m-diethylaminophenol is added in small portions. The reaction mixture is stirred at room temperature for ½ hour, then heated on a steam bath for ½ hour. ② After cooling to room temperature, the reaction mixture is poured into 1200 ml 1 molar sodium acetate and stirred for 1 hour. The solution is diluted to 2000 ml and stirred an additional 2 hours before collecting the product,* 4-diethylaminosalicylaldehyde. Brown crystals, yield 21.0 g.

*Occasionally the product remains a tar. The tar is taken up in acetic acid and twice the volume of water added to precipitate the product as a brown crystalline material.

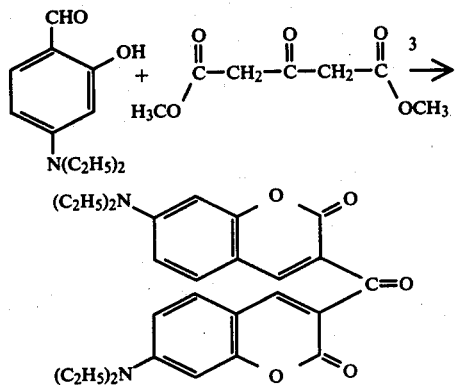

3,3'-carbonylbis(7-diethylaminocoumarin)

③ A mixture of 52.5 g (0.27 mole) 4-diethylaminosalicylaldehyde, 22.5 g (0.13 mole) dimethyl-1,3-acetonedicarboxylate, 500 ml 95 percent by volume ethyl alcohol and 30 ml piperidine is heated under reflux on a steam bath for 3 hours. After cooling, the solid is collected, washed with a small amount of ethyl alcohol, and recrystallized twice from a mixture of ethyl alcohol and acetonitrile. Yield 38.0 g.; m.p. 213° C.

PREPARATION 5

Preparation of methyl 7-diethylamino-3coumarinoylacetate.

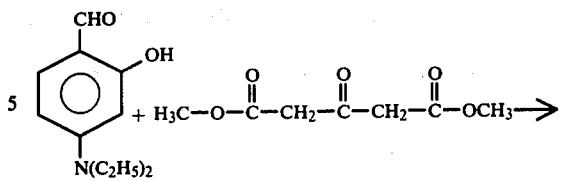

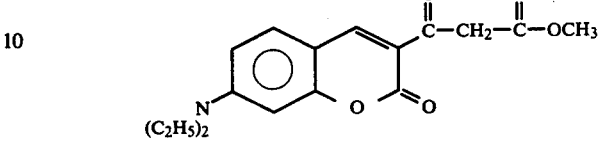

A solution of 1.93 g 4-diethylaminosalicylaldehyde, 1.80 g. dimethyl 1,3-acetone dicarboxylate in 10 ml. alcohol containing 10 drops piperidine was heated under reflux on a steam bath for 2 hours. After chilling in the freezer, the product was collected and recrystallized from a mixture of alcohol and acetonitrile. Yield 2.6 g (82%).

PREPARATION 6

Preparation of 7-diethylamino-5',7'-dimethoxy-3,3'-carbonylbiscoumarin.

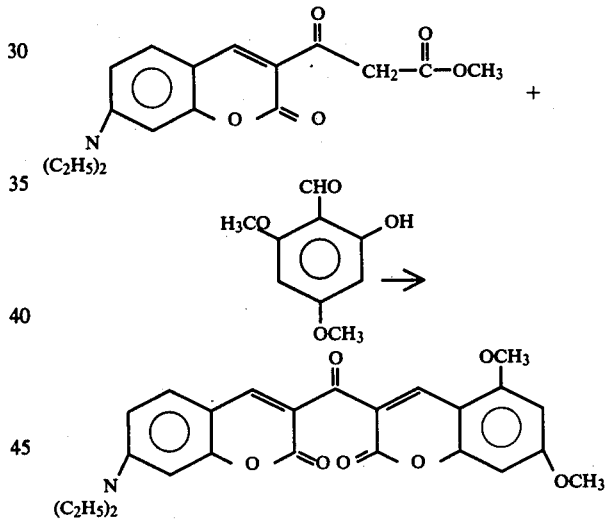

a mixture of 1.75 g methyl 7-diethylamino-3-coumarinoylacetate and 1.1 g 4,6-dimethoxysalicylaldehyde in 25 ml acetonitrile was heated until the reagents were dissolved. One and a half milliliters piperidine were added and the reaction mixture heated under reflux on a steam bath for 2 hours. After chilling in a freezer, the product was collected and recrystallized from a mixture of acetonitrile and pyridine. Yield 1.15 g (46%).

In order to use the sensitizers of our invention in an aqueous system or in an aqueous processable photoreactive polymer system, it is advantageous to incorporate in the sensitizer molecule a solubilizing group which does not substantially affect their ability to function as sensitizers. However, some shift in the absorption range may occur. Particularly useful groups include sulfonate groups and onium groups, including cyclo-onium salt groups, e.g. pyridinium, oxonium, etc.

Some of these compounds retain sufficient solubility in conventional organic coating solvents to allow them to be used in systems which require coating from organic solvents but are intended for processing with water.

The preferred compounds for such solubility are of the formulas:

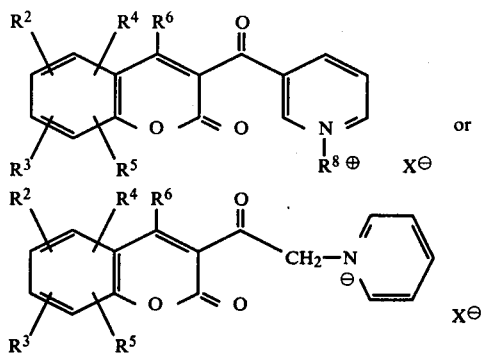

in which the values for R², R³, R⁴, R⁵, R⁶, R⁸ and X⊖ are as defined above on page 4.

PREPARATION 7

Preparation of 3-nicotinoyl-7-methoxy coumarin.

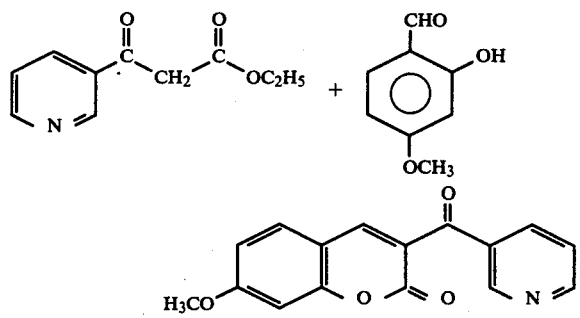

A mixture of 0.65 g ethyl nicotinoylacetate, 0.5 g 2-hydroxyanisaldehyde and 10 ml alcohol was heated on a steam bath until solution was attained. Five drops of piperdine were added and heating was continued. After several minutes the reaction mixture solidified. An additional 10 ml of alcohol were added and the reaction mixture heated another 15 minutes. After cooling, the solid was collected and recrystallized twice from a mixture of alcohol and acetonitrile.

3-(7-methoxy-3-coumarinoyl)-1-methyl pyridinium fluorosulfate.

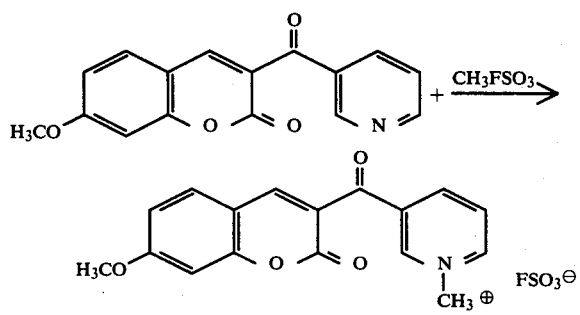

Two milliliters of methylfluorosulfonate was added to a stirred solution of 1.5 g 3-nicotinoyl-7-methoxycoumarin in 120 ml dichloromethane.

Stirred ½ hour and collected the solid. Recrystallized from alcohol. Yellow needles. Yield 1.5 g.

Calc. C, 51.6; H, 3.6; N, 3.5; S, 8.1 Found: C, 51.5; H, 3.6; N, 3.6; S, 8.5

PREPARATION 8

Preparation of 3-(5,7-diethoxy-3-coumarinoyl)-1-methylpyridinium fluoroborate.

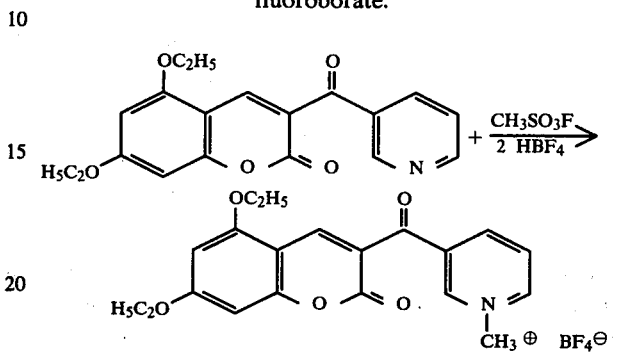

One-half milliliter of methyl fluorosulfonate was added to a stirred solution of 0.5 g. 5,7-diethoxy-3-nicotinoyl coumarin in 20 ml dichloromethane. The dichloromethane was evaporated, the residue dissolved in alcohol and 50 percent fluoroboric acid was added dropwise until precipitation was complete. After chilling, the product was collected and recrystallized from alcohol.

Calc: C, 54.4; H, 4.6; N, 3.2; Found: C, 54.5; H, 4.8; N, 3.3.

Preparation 9:
3,3'-Carbonylbis(5,7-di-n-propoxycoumarin)

3,5-Dipropoxyphenol was prepared according to the procedure of Weidel and Pollok, *Monatshaft J. Chemie*, 18, p. 347 (1897), by refluxing phloroglucinol in HCl-saturated propanol. This dipropoxyphenol was treated at room temperature with an equimolar amount of a phosphoryl chloride-dimethylformamide Vilsmeier complex in dimethylformamide. After stirring for 1 hour the mixture was poured into icewater. A semisolid material was separated and was decanted and repeatedly extracted with n-hexane. The hexane solution was concentrated and cooled in a freezer. 4,6-Dipropoxysalicylaldehyde crystallized out, yielding 43% of the theoretical amount. Condensation of the material with acetone dicarboxylic ester as described in Preparation 4 above led to 3,3'-carbonylbis(5,7-di-n-propoxycoumarin) in almost quantitative yield.

The sensitizers of this invention will sensitize any light-sensitive material selected from simple and polymeric compounds having an azide group (—N₃), or unsaturated groups e.g., olefinic >C=< groups. As used herein, "simple compound" means an oligomer or a nonpolymeric compound. The light-sensitive material and the coumarins are coated in admixture, which as used herein includes physical mixtures as well as solutions, dispersions, and the like.

Many of these materials are photopolymerizable or photohardenable. These terms "photopolymerizable" and "photohardenable" as used herein refer to systems in which the molecular weight of at least one component of the photosensitive layer is increased by exposure to actinic radiation sufficiently to result in a change in the solubility or the rheological and thermal behavior of the exposed areas.

Among suitable photopolymerizable or photohardenable systems are: (1) those in which a photopolymerizable monomer is present alone or in combination with a compatible binder, or (2) those in which the photohardenable group, within or attached to a polymer backbone, becomes activated on exposure to light and may then cross-link by reacting with a similar group or other reactive sites on adjacent polymer chains. Where the monomer or photohardenable group is capable of addition polymerization, e.g., a vinyl monomer, the photopolymerized chain length may involve addition of many similar units initiated by a single photochemical act. Where only dimerization of similar compounds is involved, e.g., cinnamoyl compounds, the average molecular weight of the photosensitive constituent can be at best only doubled by a single photochemical act.

The photopolymerizable layer can be composed of any addition-polymerizable monomer (vis., ethylenically unsaturated monomer) and coumarin sensitizer in admixture with one or more other similar monomers. The photopolymerizable layer can also contain added preformed compatible condensation or addition polymers as well as immiscible polymeric or non-polymeric organic or inorganic fillers or reinforcing agents, which are essentially transparent, e.g., the organophilic silicas, bentonites, silica, powdered glass, etc., having a particle size less than 0.4 mil and in amounts varying with the desired properties of the photopolymerizable layer. The preferred monomers are the ethylenically unsaturated, addition-polymerizable monomers, particularly those wherein the said ethylenic linkages are terminal, i.e., those monomers having the characteristic $CH_2 = C <$ group, i.e., the vinyl monomers. Because of the greater speed with which such compositions polymerize to rigid materials, it is preferred that the photopolymerizable layer contain appreciable proportions of ethylenically unsaturated polymerizable materials containing a plurality of the polymerizable linkages per molecule.

Exemplary photopolymerizable monomers include acrylic monomers, particularly bis-, tris-, etc. acrylates and methacrylates, etc. Yet another class of such light-sensitive compounds includes, for example, those having the general formula

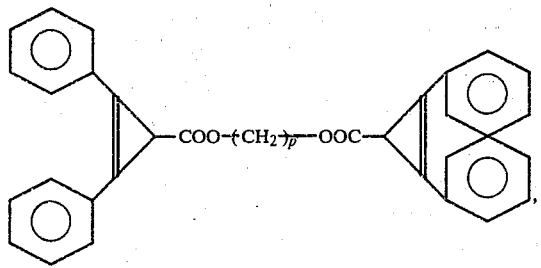

wherein p' is from 1–10, such compounds being addition-polymerizable in the presence of activating radiation and the coumarins of this invention.

The photopolymerizable layer may be composed of a polymerizable monomer and a polymerizable polymer in admixture with the coumarin sensitizer. Where a photopolymerizable molecule has more than one reactive site, a cross-linked network can be produced.

A typical crosslinkable photopolymer is disclosed in Murray U.S. Pat. No. 1,965,710 issued July 10, 1934 which describes a resist image formed from a layer of cinnamal ketone containing another resinous material which, after exposure under a design, may be selectively dissolved in the unexposed area whereby the area of the support thus based may be etched. Minsk et al U.S. Pat. Nos. 2,610,120; 2,690,966; 2,670,285; 2,670,286; and 2,670,287 respectively disclose light-sensitive photomechanical resist compositions containing polymeric materials containing combined polymeric units having $R — CH = CH — CO$ groups wherein R is an aryl group such as a phenyl, m-nitrophenyl, etc. sensitized with nitro, triphenylmethane, anthrone, quinone and ketone compounds.

Exemplary photocrosslinkable polymers include those such as cinnamylideneacetate esters of poly(vinyl alcohol), cinnamic acid esters of poly(vinyl alcohol), cinnamic acid esters of cellulose, cinnamic acid esters of hydroxyalkylcellulose, cinnamoylated polystyrene, cinnamyl vinyl ketone polymers, unsaturated polyesters, etc.

Other photopolymerizable materials which may be sensitized with the coumarins, as disclosed herein, are disclosed in Wadsworth et al U.S. Pat. No. 3,779,989 issued Dec. 18, 1973. These are light-sensitive polymers which contain a diarylcyclopropene substituent, such as a diarylcyclopropenium ion or a diarylcyclopropenyl group, directly attached to a phenyl group which in turn is attached to a polymer backbone. These polymers are useful in preparing photomechanical images and for other purposes. Alternatively, the diarylcyclopropenium ion or -cyclopropenyl group can be attached by an ester linkage to an ethyl methacrylate monomer copolymerized with other acrylate monomers.

Another class of light-sensitive polymers are disclosed in U.S. Pat. No. 3,782,938 issued Jan. 1, 1974 to DeBoer. These light-sensitive polymers have appended to a polymer backbone a light-sensitive unsaturated cyclic group which is a 3- to 6-membered carbocyclic or monocyclic heterocyclic ring containing an ethylenic double bond or a 5- to 6-membered ethylenically unsaturated carbocyclic or heterocyclic ring free of exocyclic double bonds and fused to an aromatic ring of the benzene series.

Additional light-sensitive polymers which can be sensitized with the coumarins are also disclosed in Schellenberg et al U.S. Pat. No. 3,030,208 issued Apr. 17, 1962. These light-sensitive compounds are polycondensation products predominately linked through ester bonds and having

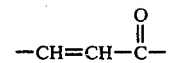

groups bonded to aromatic nuclei. Included in this class are polymers containing repeating units having the formula

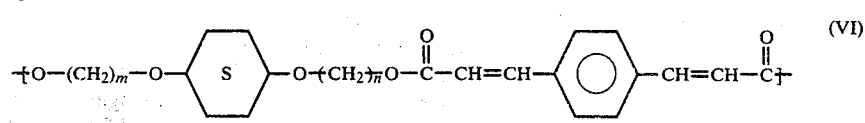

(VI)

wherein m and n are the same or different and are each equal to 1, 2 or 3; for example, m and n both equal to 2.

Other polymers sensitizable by the coumarins described above include copolymers of vinylcinnamate and vinylnaphthoate. Highly useful examples of such copolymers are disclosed and claimed in U.S. Application Ser. No. 710,992, filed August 2, 1976, now abandoned, by R. Daly and R. Engebrecht, entitled "Acid-Resistant Copolymer and Photographic Element Incorporating Same", and include polymers wherein from about 30 to about 97 mole percent of the recurring units have the general structure

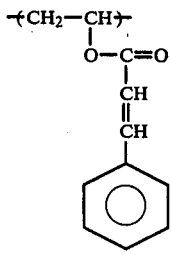
(VII)

and wherein from about 3 to about 70 mole percent of the recurring units have the general structure

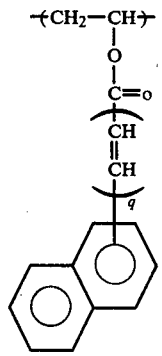
(VIII)

where q is 0 or 1; and a polymer having as repeating units the structure

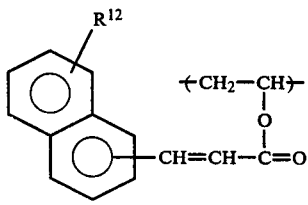
(IX)

wherein $R^{12}$ is hydrogen or lower alkyl or alkoxy containing from 1 to 5 carbon atoms.

Such acid-resistant copolymers will produce, upon exposure to light rich in UV, and development, a crosslinked copolymer resistant to hot concentrated nitric acid for a time period sufficient to provide a "deep etch" of the support underlying what was the nonexposed areas of the polymer. "Deep etch" as used herein, means an etch sufficient to remove at least 370 microns of the support. Removal of as much as 1000 microns is common. The actual time period for such acid etch will of course vary, depending upon the material comprising the support.

The above-described acid-resistant copolymers can be prepared by adding a naphthoyl acid halide or a 3-(naphthyl)-acryloyl acid halide and cinnamoyl acid halide to a suspension of poly(vinyl alcohol) (hereinafter, PVA) in a tertiary amine solvent such as pyridine, to esterify the alcohol groups. The mole ratio of added reactants is adjusted to achieve the desired mole percent of the copolymer recurring units. The sequence of addition of the acid chlorides can be modified even to the extent of adding them all together or adding first a portion of the first acid chloride, all of the second, and then the remainder of the first. Except as noted above with regard to the sequence of addition, the conditions of the reactions, such as temperatures and times, can be those well known in the art, such as those disclosed in the aforesaid U.S. Pat. No. 3,560,465, the disclosure of which is expressly incorporated herein by reference. In addition, the following preparation is set forth as a non-limiting example:

A pyridine (300 ml) suspension of 13.7 g "Elvanol 71-30-M" PVA [a medium molecular weight poly(vinyl alcohol), 100% hydrolyzed, manufactured by DuPont] was stirred at 60° C. for 16 hours to swell the polymer. The suspension was cooled to 50° C. and 28.5 g α-naphthoyl chloride was added. After stirring 6 hours at 50° C. 25 g of cinnamoyl chloride was added. Warming was continued for another 16 hours after which the solution was cooled. The reaction mixture was precipitated into water and the resultant fiberous polymer washed thoroughly with water and dried to give 41.8 g of polymer. The product was readily soluble in solvents such as cyclohexanone and 1,2-dichloroethane.

Still other photopolymerizable materials are disclosed in U.S. Pat. No. 3,929,489 issued Dec. 30, 1975 to Arcesi and Rauner entitled "Lithographic Plates Having Radiation Sensitive Elements Developable With Aqueous Alcohol."

In another useful embodiment of the invention the photopolymerizable material sensitizable by the coumarins described above has incorporated into the polymer molecule disulfonamido units having the structural formula:

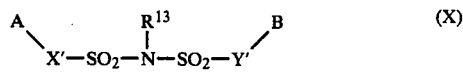
(X)

wherein
(a) $R^{13}$ is selected from the group consisting of —H and an alkali metal,
(b) X' and Y' are the same or different radicals selected from the group consisting of arylene radicals of 6 to about 12 carbons and said radicals being unsubstituted or substituted with chlorine atoms, and
(c) A and B are the same or different and are selected from the group consisting of

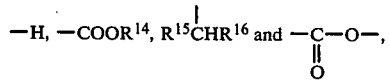

wherein
$R^{14}$ is selected from the group consisting of —H, alkyl of from 1 to about 8 carbon atoms, alkylene of from 2 to about 8 carbon atoms, and aryl of from 6 to about 14 carbon atoms; and
$R^{15}$ is hydrogen or alkyl of from 1 to about 8 carbon atoms and $R^{16}$ is hydrogen, alkyl or from 1 to about 8 carbon atoms so that at least one of A and B has a valence of 1 as disclosed in Caldwell et al U.S. Pat. No. 3,546,180 issued Dec. 8, 1970.

Unsaturated radiation-decomposable vesiculating agents capable of generating a gas upon imagewise exposure which can be sensitized by coumarins include the vesiculating agents of G. L. Fletcher, D. H. Wadsworth and J. E. Jones, in U.S. Application Ser. No. 739,744 entitled *Cyclopropenone Vesicular Imaging Composition Element and Process*, filed Nov. 8, 1976.

These vesiculating agents release a gas upon exposure to light. When incorporated in a heat-deformable, relatively gas impermeable film coating, exposed to actinic radiation, and heated, the gas is released upon exposure and allowed to expand on heating because of the softened matrix which is deformed by gas expansion. Upon cooling, the exposed areas are permanently deformed and opaque to the transmission of light, thus images can be viewed by projection if coated on a transparent support. If coated on an opaque substrate, the image appears white, when viewed by reflected light.

Preferred radiation-decomposable vesiculating agents are cyclopropenones having the formula

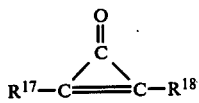

wherein $R^{17}$ and $R^{18}$ are the same or different and are each a substituted or unsubstituted aryl radical containing from 6 to 10 carbon atoms in the aromatic ring, such as, for example, phenyl and naphthyl; or an aralkenyl radical having 6 to 10 carbon atoms in the aryl portion and 1 to 5 carbon atoms in the alkenyl portion, for example 2,2-diphenylvinyl, 2-phenylvinyl, 2-naphthylvinyl and the like;

the substituents of each of the substituted aryl radical being one or more radicals selected from the group consisting of, in any position on the aryl ring:

(1) alkyl or alkoxy radicals containing from 1 to 5 carbon atoms, for example, methyl, ethyl, propyl, iso-propyl, butyl, methoxy, ethoxy, propoxy, butoxy and the like;

(2) a nitro radical;

(3) an aryloxy radical containing from 6 to 10 carbon atoms, for example phenoxy and naphthoxy and the like;

(4) a halogen, for example chlorine, fluorine and the like; and (5) a homopolymer or copolymer to which the aryl radical is attached as a dependent moiety, the polymer having at least one repeating unit containing the formula $-R^{19}-)_a$ wherein $R^{19}$ is a lower alkylene radical containing from 1 to 5 carbon atoms, for example vinylene, propylene, and the like, and "a" is at least a portion of the number of repeating units in a given polymer chain.

Thus, $R^{17}$ and $R^{18}$ can each be any one of the following formulas:

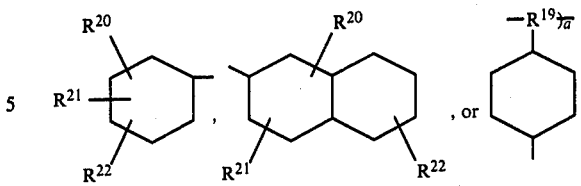

where $R^{20}$, $R^{21}$, and $R^{22}$ are the same or different and are any of the substituents defined above as (1), (2), (3) or (4); and $R^{19}$ is the repeating unit defined above.

The above cyclopropenones can be prepared by known processes, of which the following preparation of 2-(2-methoxynaphthyl)-3-phenylcyclopropenone is illustrative only:

A mixture of 14.0 g (0.11 mole) of anhydrous aluminum chloride and 17.8 g (0.10 mole) of tetrachlorocyclopropene in 200 ml of 1,2-dichloroethane is stirred at room temperature for one hour. The mixture is cooled to 0° C. and treated with 7.8 g (0.10 mole) of benzene, maintaining the temperature between 0° and 5° C. Upon completion of the addition, the reaction mixture is warmed slowly to 50° C., re-cooled to −25° C., and treated with a solution of 15.8 g (0.10 mole) of 2-methoxynaphthalene is 1,2-dichloroethane, maintaining the temperature between −25° and −20° C. Upon completion of the addition, the reaction mixture is allowed to warm to room temperature, and treated with ice and ice-water. The organic layer is separated, stripped in vacuo, and the resulting residue recrystallized from mdthanol to furnish 17.5 g of product, 2-(2-methoxynaphthyl)-3-phenylcyclopropenone.

In a particularly useful embodiment, a polymeric binder is employed with the vesiculating cyclopropenone. Any binder useful with vesiculating agents can be used. Included here are polysulfonamides such as those described in *Research Disclosure*, Vol. 131, Publication No. 13107, Mar. 1975, published by Industrial Opportunities Ltd, Homewell, Havant Hampshire P091EF United Kingdom and also poly(vinyl chloride), poly(vinylidene chloride), polystyrene; and copolymers obtained by copolymerizing acrylonitrile with vinyl chloride, styrene, vinylidene chlorofluoride, or 1,1-difluoroethylene; by copolymerizing vinyl chloride with methyl acrylate, acrylic acid, diethyl maleate, or vinyl acetate; or by copolymerizing vinylidene chloride with vinyl chloride, vinyl acetate, vinyl alcohol, ethyl acrylate, or acrylonitrile. Examples of the homo- or co-polymerization of vinylidene chloride are described in U.S. Pat. No. 3,032,414 issued to R. James. Still other useful binders include α-chloroacrylonitrile preferably mixed with other copolymers, as disclosed for example in U.S. Pat. No. 3,620,743, and Bisphenol A/epichlorohydrin copolymer, wherein "Bisphenol A" means 4,4'-isopropylidene diphenol.

Azides which can be sensitized by the compounds of the invention include the poly(vinyl azidobenzoates) and poly(vinyl azidophthalates) of U.S. Pat. Nos. 2,948,610; 3,002,003; and 3,096,311. Highly useful forms include those wherein the recurring polymeric units are represented as in formula (IV) above,

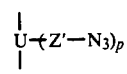

in which U represents the atoms of a recurring group in the polymer chain proper, Z' is a linkage joining the azide group to the recurring atoms of the polymer chain, for example, the atoms and groups —CH$_2$—COphenylene, —C$_6$H$_4$—CH$_2$—O—CO—, —C$_6$H$_4$—CO—O—, —C$_6$H$_4$—O—, —C$_6$H$_3$(COOH)—CO—O—, —C$_6$H$_4$—O—C$_2$H$_4$—O—; and p is 1 or 2. In copolymers, additional polymeric units U$_1$, U$_2$ etc., which can be the same as or different from U, are present and the copolymers can therefore be represented as

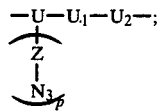

p having the values described above.

If the polymer contains recurring units of the structure

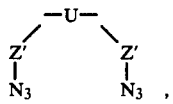

the Z''s can be the same or different linkages such as the linkage mentioned above. They may be present, for example, in aryl azide derivatives of hydrolyzed cellulose esters in which case two or more azide groups can be adjoined to a single recurring polymeric unit of the cellulosic chain. Similarly, more than one azide group can be attached to Z' as in the case of a diazidophenyl group.

The inherently light-sensitive alkali soluble azide polymers particularly efficacious for use contain recurring units of the formula

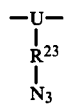

in which R$^{23}$ is a bivalent aromatic radical of the benzene series whose free valences do not necessarily belong to the aromatic nucleus, for example, phenylene,

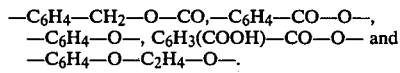

If an acid group is used in the inherently light-sensitive alkali soluble azide polymer, such as a carboxyl group, it need not be attached to the recurring polymeric unit containing the azide group, but may be present on some other recurring unit of the polymer, for example, as in the case of the maleic acid azidostyrene copolymer described hereinafter. In the vinyl azidophthalate copolymers described hereinafter, the carboxyl group is attached directly to the aromatic nucleus bearing the azide group.

Useful light-sensitive film-forming azidostyrene homopolymers contain the following recurring structural unit:

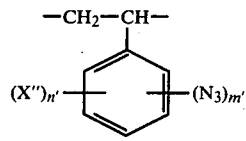

or copolymers of said azidostyrene consist of the following recurring structural units in random combination:

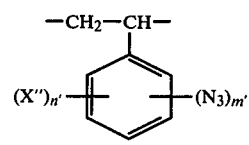

wherein the ratio of XIII(a) units to XIII(b) units in each resin molecule can vary from 1:19 to 19:1, i.e., XIII(b) are present from 5 to 95 mole percent, and wherein m' represents in each instance a digit 1 or 2, n' represents a digit from 0 to 2, X'' represents a chlorine atom, an alkyl group containing from 1 to 4 carbon atoms, e.g., methyl, ethyl, propyl, butyl, etc., an alkoxy group containing from 1 to 4 carbon atoms, e.g., methoxy, ethoxy, propoxy, butoxy, etc., and a nitro group, and R$^{24}$ represents an ethyleneically unsubstituted polymerizable material such as ethylene, isobutylene, a 1,3-butadiene, styrene and substituted styrenes, etc., an $\alpha,\beta$-unsaturated mono- or di-carboxylic acid unit such as acrylic acid, an $\alpha$-alkylacrylic acid, maleic acid, citraconic acid, itaconic acid, etc., and the anhydrides, alkyl esters, imides, N-alkyl imides, nitriles, amides, and N-alkyl and N,N-dialkyl substituted amides of these acids, fumaric and mesaconic acids and their alkyl esters, nitriles, amides and N-alkyl and N,N-dialkyl substituted amides, vinyl alkyl ketones such as vinyl methyl ketone, vinyl halides such as vinyl chloride, vinylidene halides such as vinylidene chloride, and the like units, and wherein in each instance in the above the alkyl and alkoxy groups contain from 1 to 4 carbon atoms.

In using the light-sensitive material sensitized in the manner of our invention in connection with the preparation of lithographic or relief image plates, the plates are prepared by coating a solution of light-sensitive polymer and a sensitizer of the invention on a suitable support such as a metal place or flexible film support such as polyester. After drying, the plate is exposed through a line pattern whereby the polymer in the exposed areas becomes cross-linked and solvent insoluble.

Of particular interest is the use of lasers, such as ultraviolet-tuned lasers or visible-tuned lasers, as a light source. For instance, an Argon ion laser can provide an ultra-violet source at 351 and 364 nm or a visible output at 488 and 515 nm. A single coumarin sensitizer may be used. However, a combination of coumarin sensitizers of our invention or a combination of a one or more coumarin sensitizers with one or more other sensitizers may provide increased speeds. For instance, many crosslinkable polymers, can be best sensitized at 488 nm with 3,3'-carbonylbis(7-diethylaminocoumarin). The response of this sensitizer at 350-370 nm, however, is not optimum. 3-Benzoyl-7-methoxycoumarin gives higher speeds in this range. However, a mixture of both compounds increases the photographic speed in the 350–370 nm. range over that sensitized with 3,3'-carbonylbis(7-diethylaminocoumarin) alone, without affecting the long wavelength response of the system. An exposed plate is then bathed in a suitable solvent to remove the non-crosslinked polymer in the unexposed areas. Such a plate can be used with a laser tuned either in the range 351–364 nm. or in the range 488–515 nm.

Useful solvents include 1,2-dichloroethane, chlorobenzene, 2-ethoxyethyl acetate, cyclohexanone, water, alcohol, a 20:80 by weight mixture of 2-methoxyethyl acetate and xylene, etc.

Suitable support materials can be chosen for any of the embodiments of the invention from among a variety of materials which do not directly chemically react with the coating composition. Such support materials include fiber base materials such as paper, polyethylene-coated paper, polypropylene-coated paper, parchment, cloth, etc.; sheets and foils of such metals as aluminum, particularly grained aluminum, anodized aluminum or grained and anodized aluminum, copper, magnesium, zinc, etc.; glass and glass coated with such metals as chromium, chromium alloys, steel, silver, gold, platinum, etc.; synthetic resin and polymeric materials such as poly(alkyl acrylates), e.g. poly(methyl methacrylate), polyester film base—e.g. poly(ethylene terephthalate), poly(vinyl acetals), polyamides—e.g. nylon and cellulose ester film base—e.g. cellulose nitrate, cellulose acetate, cellulose ester with a hydrolyzed surface, cellulose acetate propionate, cellulose acetate butyrate and the like.

The optimum coating thickness of the radiation-sensitive layer will depend upon such factors as the use to which the coating will be put, the particular light-sensitive material employed, and the nature of other components which may be present in the coating. Typical coating thicknesses can be from about 0.05 to 10.0 microns or greater, with thicknesses of from 0.1 to 2.5 microns being preferred for lithographic printing plate applications.

The amount of sensitizer which must be present need only be that which is sufficient to appreciably increase the speed of the composition beyond that which is possible without any sensitizer. As used herein, "appreciably increase" means, a speed which is at least about 1.5 times as fast as the composition that lacks a sensitizer. The actual amount will vary, of course, depending upon the material being sensitized, the thickness of the coating and upon other factors such as the light source used. These factors are well understood by the artisan and need not be delineated further. Generally, the sensitizers of the invention are employed at a concentration of about $3 \times 10^{-6}$ to about $6 \times 10^{-4}$ moles of sensitizer per gram of light-sensitive material or about 0.1 to about 20 percent by weight of the light-sensitive material, preferably about 1 to 11 percent.

The results recorded in the examples that follow were obtained with the general procedure described below, unless otherwise stated:

In each Example 1-11, $6 \times 10^{-5}$ mole of sensitizer is dissolved in 10 ml of a 2 percent solution of the light-sensitive polymer in cyclohexanone. Five milliliters of this solution is spin-coated on aluminum. Identical, freshly prepared coatings, using equimolar amounts of 2-benzoylmethylene-1-methyl-β-naphthothiazoline are used as a control.

Strips of the dried coatings are exposed through a 0.15 O.D. incremented step wedge and developed by dissolving away the non-crosslinked polymer in a tray of 1,2-dichloroethane.

Light sources which may be used include broad spectrum light sources, filtered or unfiltered, including Xenon or carbon arcs, narrow spectrum sources such as mercury lamps and lasers which emit within low (uv) to medium (visible light) wavelengths.

Three different light sources are used in the following examples:
  A. Ozamatic source - a commercial unit which uses a full spectrum, high pressure mercury lamp.
  B. 366 nm - The wavelength of the mercury line isolated by filtration of a high pressure mercury lamp.
  C. 3500 A - A laboratory built exposure device containing an arrangement of Rayonet photochemical reactor lamps whose emission maximum is at 350 nm.
  D. 405 nm - The wavelength of the mercury line isolated by filtration of a high pressure mercury lamp.
  E. 436 nm - The wavelength of the mercury line isolated by filtration of a high pressure mercury lamp.

The light-sensitive polymer used in all of the samples in Examples 1-4 was poly(vinyl cinnamate). In Example 5, the polymer was poly(vinyl acetate-co-vinyl p-azidobenzoate). In Examples 6-9 and 11, the polymer was a modified poly(vinyl alcohol) consisting of 20 percent free hydroxyl groups, 12 percent acetate groups, 37 percent 2,3-diphenylcyclopropenecarboxylate groups, and 31 percent benzoate groups.

In Example 10, the polymer was poly(vinylacetate-co-vinylbenzoate-co-vinyl cinnamylideneacetate). (mole ratio 12:38:50)

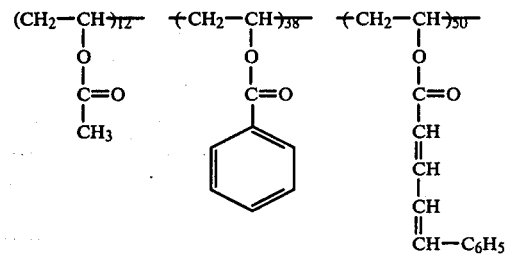

The following examples are included for a further understanding of the invention:

EXAMPLE 1—Light Source: A

| Sensitizer | Relative Speed |
| --- | --- |
| 2-benzoylmethylene-1-methyl-β-naphthothiazoline (BNTZ) (control)* | 1 |
| 3-benzoyl-5,7-dimethoxycoumarin | 1 |
| 3-benzoyl-7-methoxycoumarin | 1 |
| 3-benzoyl-6-methoxycoumarin | 1/2 |
| 3-benzoyl-8-ethoxycoumarin | 1/4 |
| 3-benzoylcoumarin | 1/6 |
| 3-(p-nitrobenzoyl)coumarin | 1/4 |
| 5,7,7'-trimethoxy-3,3'-carbonylbiscoumarin | 1.75 |
| 3,3'-carbonylbis(5,7-dimethoxycoumarin) | 1.75 |

*In this and the remaining examples, the respective light-sensitive polymer sensitized with 2-benzoylmethylene-1-methyl-β-naphthothiazoline served as the control. For comparative purposes, this combination is assigned a relative speed of one. It is 350 to 500 times faster than unsensitized poly(vinyl cinnamate).

EXAMPLE 2—Light Source: C

| Sensitizer | Relative Speed |
| --- | --- |
| 2-benzoylmethylene-1-methyl-β-naphthothiazoline (control) | 1 |
| 3-benzoyl-5,7-dimethoxycoumarin | 2 |

EXAMPLE 3—Light Source: A

| Sensitizer | Relative Speed |
| --- | --- |
| 2-benzoylmethylene-1-methyl-α-naphthothiazoline (control) | 1 |
| 3-benzoylbenzo[f]coumarin | 0.6 |
| 3,3'-carbonylbis(7-methoxycoumarin) | 1.2 |
| 3-cyano-7-methoxycoumarin | 0.1 |
| 3,3'-carbonylbis(6-methoxycoumarin) | 0.8 |

EXAMPLE 4—Light Source: B

| Sensitizer | Relative Speed |
| --- | --- |
| 2-benzoylmethylene-1-methyl-β-naphthothiazoline (control) | 1 |
| 3-benzoylbenzo[f]coumarin | 2 |

EXAMPLE 5—Light Source: A

| Sensitizer | Relative Speed |
| --- | --- |
| none (control) | (1) |
| 5,7,7'-Trimethoxy-3,3'-carbonylbiscoumarin | 40* |
| 3,3'-Carbonylbis(7-diethylaminocoumarin) | 10 |

*This corresponds to a speed 4 times faster than that of poly(vinyl cinnamate) sensitized with BNTZ.

EXAMPLE 6—Light Source: C

| Sensitizer | Relative Speed |
| --- | --- |
| 2-benzoylmethylene-1-methyl-β-naphthothiazoline (control) | 1 |
| 3-benzoyl-5,7-dimethoxycoumarin | 2 |
| 3-benzoyl-7-methoxycoumarin | 2 |
| 3-acetyl-7-methoxycoumarin | 1.4 |
| 3-benzoyl-7-methoxycoumarin | 2 |
| 3-acetyl-7-methoxycoumarin | 2 |
| 3-benzoyl-6-bromocoumarin | 0.7 |
| 3,3'-carbonylbiscoumarin | 1.2 |

EXAMPLE 7—Light Source: A

| Sensitizer | Relative Speed |
| --- | --- |
| 2-benzoylmethylene-1-methyl-β-naphthothiazoline (control) | 1 |
| 5,7,7'-Trimethoxy-3,3'-carbonylbiscoumarin | 1.75 |
| 3,3'-Carbonylbis(5,7-dimethoxycoumarin) | 1.7 |
| 7-(1-Pyrrolidinyl)-3-thenoylcoumarin | 1.4 |

EXAMPLE 8

| | Light Source | Relative Speed (BNTZ=1) |
| --- | --- | --- |
| 3-benzoyl-7-dimethylaminocoumarin | A | 0.8 |
| 3-benzoyl-7-dimethylaminocoumarin | D | 0.7 |
| 3-benzoyl-7-dimethylaminocoumarin | B | 0.5 |
| 7-diethylamino-4-methylcoumarin* | A | 0.2 |

*This is a control for comparison - it is not a sensitizer of this invention.
**BNTZ = 2 benzoylmethylene-1-methyl-β-naphthothiazoline.

EXAMPLE 9

| | Light Source | Relative Speed (BNTZ=1) |
| --- | --- | --- |
| 3,3'-carbonylbis(7-diethylaminocoumarin) | A | 1.0 |
| | E | 2.0 |
| | D | 0.7 |
| | B | 1.0 |

EXAMPLE 10

| | Light Source | Relative Speed (BNTZ=1) |
| --- | --- | --- |
| 3,3'-carbonylbis(7-diethylaminocoumarin) | A | 1.2 |
| | E | 2.5 |

| Sensitizer | Light Source | Relative Speed (BNTZ=1)* |
| --- | --- | --- |
| 3-(4-ethoxycinnamoyl)-7-methoxycoumarin | A | 0.33 |
| | B | 0.5 |
| 3-[(3-methylbenzothiazol-2-ylidene)acetyl]coumarin | A | 0.025 |
| | B | 0.025 |
| 3-(1-adamantoyl)-7-methoxycoumarin | A | 0.2 |
| | B | 1.0 |
| 3,3'-carbonylbis(7-acetoxycoumarin) | A | 0.4 |
| | B | 2 |
| 7-methoxy-3-phenylsulfonylcoumarin | A | 0.25 |
| 1,4-bis(7-diethylamino-3-coumarylcarbonyl)benzene | A | 0.22 |
| 7-methoxy-3-(p-nitrobenzoyl)coumarin | A | 0.30 |
| 3-nicotinoyl-7-methoxycoumarin | A | 2.1 |
| 3(2-benzofuranylcarbonyl)-7-methoxycoumarin | A | 0.9 |
| 3-[3-(p-ethoxyphenyl)acryloyl]-7-methoxycoumarin | A | 0.3 |

*BNTZ = 2-benzoylmethylene-1-methyl-β-naptholthiazoline

EXAMPLE 12

3,3'-Carbonylbis (7-diethylamino coumarin) ($4 \times 10^{-5}$ mole) is dissolved in 10 ml of a 2.1% dichloroethane solution of a light sensitive polymer, poly(1,4-cyclohexylenebis(oxyethylene) 1,4-phenylenediacrylate).

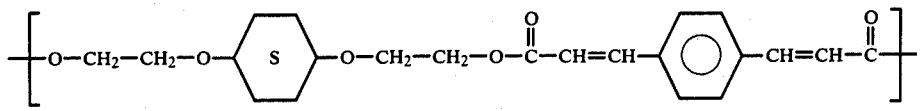

5 milliliters of this solution is spin-coated on aluminum.

A second coating was prepared identical to the first but containing $4 \times 10^{-5}$ mole 3-benzoyl-7-methoxy coumarin instead of 3,3'-carbonylbis (7-diethylaminocoumarin).

A third coating was prepared identical to the first but containing $6 \times 10^{-5}$ mole of 2-benzoylmethylene-1-methyl-$\beta$-naphthothiazoline instead of 3,3'-carbonylbis(7-diethylaminocoumarin).

The coatings were exposed in the usual manner but developed by swab developement for 15 seconds with a developer similar to that described in Example 3 of U.S. Pat. 3,707,373 issued Dec. 26, 1972 to Martinson et al and rinsed with water. Standard inking techniques may be used for better visibility of the image.

Light Source: A

| Sensitizer | Relative Speed |
|---|---|
| 2-benzoylmethylene-1-methyl-$\beta$-naphthothiazoline | 1.0 |
| 3,3'-carbonyl bis(7-diethylaminocoumarin) | 1.8 |
| 3-benzoyl-7-methoxycoumarin | 1.0 |

EXAMPLE 13 Utility in a vesicular imaging system

A dope comprising

| | |
|---|---|
| 0.75 g | polymeric polysulfonamide binder |
| .20 g | 2-(4-methoxy phenyl)-3-phenylcyclopropenone |
| 3.08 g | acetone |
| 3.08 g | 2-methoxyethanol | is coated at a 4 mil wet thickness on subbed poly(ethylene terephthalate) at a coating block temperature of 27° C. After normal drying at 49° C., the coating is "flash dried" for 10 seconds at 65° C.

A second coating, identical to the first, is prepared except that 14 mg BNTZ is added to dope.

A third coating, identical to the first, is prepared except that 15 mg 3-benzoyl-7-methoxycoumarin is added to the dope.

The coatings are exposed for identical times through a 0.15 density step tablet to a 400 watt mercury arc lamp and developed for 1 second at 150° C.

The H & D curve is plotted and the relative speeds are calculated from the differences in the log exposure at an optical density of 1.

| Coating | Relative Speed |
|---|---|
| Unsensitized coating | 1 |
| BNTZ sensitized coating | 2 |
| 3-Benzoyl-7-methoxycoumarin sensitized coating | 1.6 |

EXAMPLE 14

3,3'-Carbonylbis(7-diethylaminocoumarin) was compared to 7-dimethylamino-4-methylcoumarin in a Photopolymerizable Coating, as described in Example 10 of Wagner et al U.S. Pat. Application Ser. No. 521,617 filed Nov. 6, 1974.

A dope comprising:
a. 10 ml of a 10% dichloromethane solution of the following polymer:

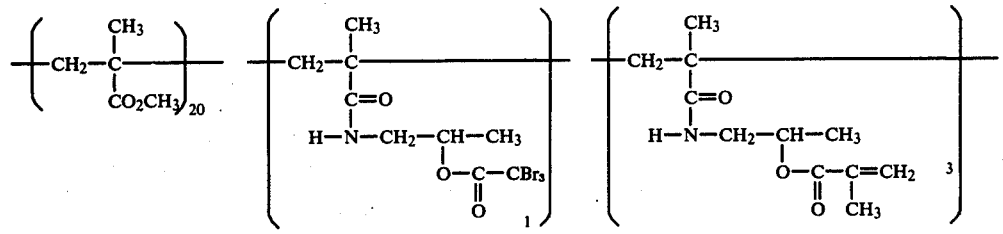

Inherent viscosity 0.21 in cyclohexanone, polystyrene equivalent molecular weight of the polymer, about 25,000 to 30,000.

b. 0.5 ml of a 10% dichloroethane solution of benzene chromium tricarbonyl, c. 0.15 g. of a plasticizer of the following structure:

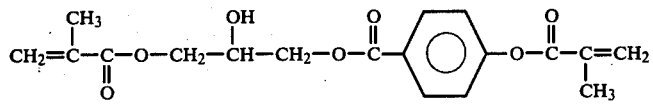

d. 10 ml of dichloroethane, e. 0.040 g 7-dimethylamino-4-methylcoumarin, was whirl-coated on grained anodized aluminum. The dried coating was overcoated with an aqueous 10% solution of a 2% succinoylated poly(vinyl alcohol) as described in Research Disclosure, Vol. 148, August 1976, Publication No. 14848, published by Industrial Opportunities Ltd., Homewell, Havant Hampshire PO91EF, United Kingdom.

A second coating was prepared identical to the first with the exception that 3,3'-carbonylbis(7-diethylaminocoumarin) was used in place of the 7-dimethylamino-4-methylcoumarin.

Both coatings were eposed for 1 minute to a 1000 watt Xenon wedge spectrograph.

The coatings were then heated for 7 seconds at 124° C. on a hot block.

The exposed coatings were swab-developed with an alkaline ethanolic aqueous developer. The images were hand inked.

The coating containing 7-dimethylaino-4-methylcoumarin showed no increase in speed and no increase in spectral sensitivity range beyond that of a typical unsensitized coating.

The coating containing 3,3'-carbonylbis(4-diethylaminocoumarin) extended the spectral sensitivity range from 430 nm to 540 nm thereby improving the overall speed of the coating by rendering it sensitive to visible light.

EXAMPLE 15

A coating identical to the second coating of Example 14 was whirler coated on grained phosphoric anodized aluminum and overcoated as in Example 14.

The dried coating was laser exposed at 488 nm and required $2 \times 10^4$ ergs/cm$^2$. It was heated and processed as in Example 14. The image was hand inked.

A coating identical to the first coating of Example 14 failed to produce an image when laser exposed at 488 nm.

EXAMPLE 16

A solution of 1 g. of 2-hydroxy-3-methacryloyloxypropyl-4-methacryloyloxybenzoate having the formula:

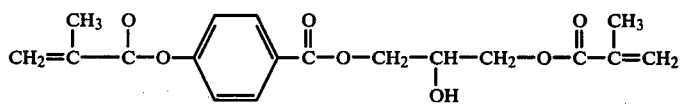

1 g. of poly(methyl methacrylate-co-ethyl acrylate-comethacrylic acid) (weight ratio 51.6:34.4:14), and 0.1 g. of 3-benzoyl-7-methoxycoumarin in 5 ml of methyl ethyl ketone was coated on copper clad epoxy fiberglass printed circuit board at a wet thickness of 0.008 in. at 43° C., air dried 5 minutes and baked at 80°-90° C., for 5 minutes. The cooled element was exposed in a Colight M-99 Printer for 2 minutes under a 0.15 O.D. incremented step wedge and developed by spraying with aqueous 4% sodium carbonate solution for 1 minute and rinsing with tap water for 1 minute to produce a resist image. Three steps developed. When a sensitizer mixture of 0.1 g. benzophenone and 0.1 g. Michler's ketone was used in place of the coumarin compound, six steps developed. A control with no sensitizer did not produce any developed steps.

These results illustrate the capability of coumarin sensitizers of our invention to sensitize photopolymerizable compositions.

EXAMPLE 17

The following coating compositions were prepared:

$6 \times 10^{-5}$ mole coumarin sensitizer 10 ml of 2% by weight solution in 4-butyrolactone:ethoxyethyl acetate (1:3 by weight) of the polymer used in Example 11

Five milliliters of this solution was spin-coated on aluminum. Identical, freshly prepared coating using equimolar amount of BNTZ was used as a control.

Strips of the dried coatings were exposed to a high pressure mercury lamp through a 0.15 O.D. incremented step wedge and developed by swabbing with KODAK "Polymatic LN" Developer. The developed strips were inked for better visibility of the images.

The following results were obtained:

| Sensitizer | Relative Speed |
|---|---|
| BNTZ | 1 |
| 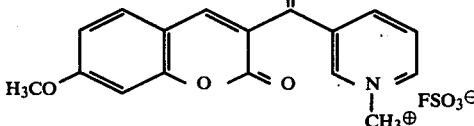 | 0.85 |
| 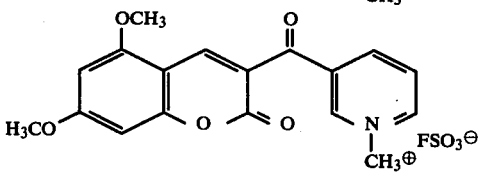 | 0.65 |

EXAMPLE 18

The following coating compositions were prepared:

$6 \times 10^{-5}$ mole coumarin sensitizer 10 ml of 2% by weight solution in cyclohexanone of the polymer used in Example 11

The solution was coated, exposed and compared to a control coating as in Example 17 with the following results:

| Sensitizer | Relative Speed |
|---|---|
| BNTZ | 1 |
| 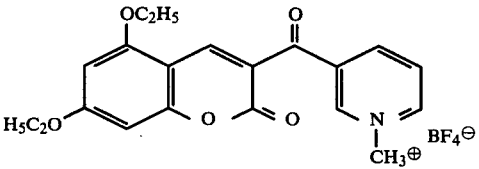 | 0.45 |

EXAMPLE 19

A dope comprised of 1 g of a light sensitive polymer of the following structure

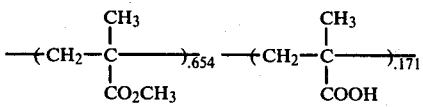

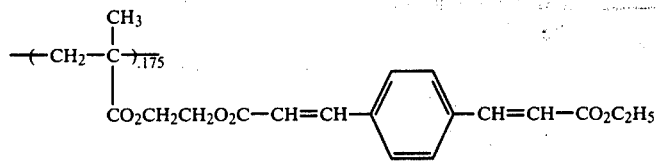

and 0.01 g of a sensitizer of the following structure

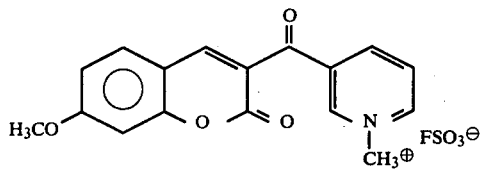

in 18 ml dichloroethane and 2 ml dimethyl formamide was spin coated at 150 rpm on a subbed aluminum plate. A portion of the plate was exposed for 4 minutes through a KODAK T-14 control scale on an "Xposer I" (Colight, Inc.). The exposed plate was developed by swabbing with Kodak "MX854-3 Polymatic LP" developer, an alcoholic basic developer available from Eastman Kodak, and inked. The speed is 0.7X the speed of a comparative plate containing BNTZ as a sensitizer.

A second portion of the plate was exposed in the same manner and developed using 90 percent water, 5 percent methanol and 5 percent ammonium hydroxide.

EXAMPLE 20

The following samples (A-H) were prepared by whirl coating cyclohexanone solutions containing 2% of the polymer used in Example 11 and the sensitizers 3,3'-carbonylbis(7-diethylaminocoumarin) and/or 3-benzoyl-7-methoxycoumarin at the concentration of 3 or $6 \times 10^{-3}$M on subbed aluminum.

The samples were exposed to unfiltered Hg-high pressure lamp through step tablets. The wedge diagrams were obtained using a Xenon arc. LN developer was used to develop the exposed plates.

Sample B, which has a lower concentration of 3,3'-carbonylbis(7-diethylaminocoumarin), was almost twice as fast as A. The coatings C and D showed similar response. Of the mixed-sensitized coatings (E-H) sample G showed the highest response at 350-370 nm and at 488 nm. The speed of sample G at 488 nm was equal to that of B and at 350-370 nm, it showed a speed similar to that of C. Using the Hg-high pressure lamp exposure the mixed sensitized sample (G) was the highest in speed. It showed a speed 1 ¼ times that of B.

EXAMPLES 21-30

A photoresist stock composition was prepared as follows:

An amount of 1.0 g of

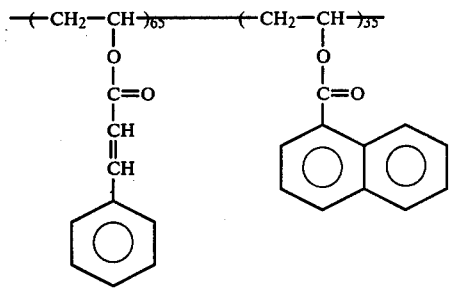

was added to 1.12 g of 4-butyrolactone 7.87 g of 2-ethoxy-ethyl acetate, and 0.01 g of hydroquinone. The sensitizers listed in the Table below were added to 10 ml portions of the stock solution. Each test solution was then whirl-coated on a magnesium "Deep-etch" plate at 100 rpm. Coated plates were pre-baked for 15 minutes at 80° C. (Average dry coating thickness was approximately 0.095 mil). All samples were exposed to a 400-watt Hg-Vapor lamp for 30 seconds through a Kodak T-14 step wedge and developed for 30 seconds in hot trichloroethylene to remove unexposed portions. Results were as follows:

Table

| Example | Sensitizer | Sensitizer Amount (Moles) | Photographic Speed Result |
|---|---|---|---|
| 21 | 3,3'-carbonylbis(5,7-di-n-propoxycoumarin) | 0.0125 | 6 |
| 22 | " | 0.025 | 7 |
| 23 | " | 0.050 | 7+ |
| 24 | " | 0.100 | 7 |
| 25 | " | 0.200 | 6 |
| 26 | BNTZ (Control) | 0.0125 | 4⁻ |

| Sample | Concentration of the sensitizer (in $10^{-3}$ M) in the coating solution | |
|---|---|---|
| | [(C₂H₅)₂N-coumarin-CO-coumarin-N(C₂H₅)₂ structure] | [H₃CO-coumarin-CO-C₆H₅ structure] |
| A | 6 | — |
| B | 3 | — |
| C | — | 6 |
| D | — | 3 |
| E | 6 | 6 |
| F | 6 | 3 |
| G* | 3 | 6 |
| H | 3 | 3 |

*A similar coating containing Michler's ketone instead of 3-benzoyl-7-methoxycoumarin also increased the response of the plate in the 350-370 nm range as compared to that of (B).

Table-continued

| Example | Sensitizer | Sensitizer Amount (Moles) | Photographic Speed Result |
|---|---|---|---|
| 27 | " | 0.025 | 5 |
| 28 | " | 0.050 | 5+ |
| 29 | " | 0.100 | 5− |
| 30 | " | 0.200 | 3 |

(1)Speed is taken as the highest number of solid steps produced in the resist layer by the given exposure through the T-14 step wedge. The largest number denotes the highest speed value. Pluses and minuses have the ususal meaning, namely slightly greater and slightly less than, respectively, the full numerical value.

The above data indicate that the coumarin of the invention is a better sensitizer than BNTZ for the tested polymer. It should be noted that a higher solids concentration of polymer and sensitizer could be used when the photoresist solution is to be roller-coated onto a magnesium plate, to achieve similar photographic speed results.

EXAMPLES 31-32

The procedure described in Example 8 was repeated, using only light source A and a different batch of the modified poly(vinyl alcohol) having however the same percent hydroxyl and acetate groups, etc. The sensitizers used and the relative speeds obtained are shown in the following table:

| Ex. | Sensitizer | Relative Speed* |
|---|---|---|
| 31 | none | about 0.013 |
| 32 | 7-diethylamino-3-(4-dimethylaminobenzoyl)coumarin | 1.25 |

EXAMPLES 33-35

The procedure of Ex. 31-32 were repeated. The sensitizers used and the relative speeds obtained are shown in the following table:

| Ex. | Sensitizer | Relative Speed* |
|---|---|---|
| 33 | none | about 0.013 |
| 34 | 7-methoxy-3-phenyl-sulfonylcoumarin | 0.25 |
| 35 | 7-methoxy-3-phenyl-sulfinylcoumarin | 0.16 |

EXAMPLES 36-39

The procedures of Ex. 31-32 were repeated, except that the amounts of the sensitizers of Ex. 37 and 38 were $4 \times 10^{-5}$ moles each, due to their lower solubility. The sensitizers used and the relative speeds obtained are shown in the following table:

| Ex. | Sensitizer | Relative Speed* |
|---|---|---|
| 36 (control) | none | about 0.013 |
| 37 | N-(7-methoxy-3-coumarinoylmethyl)-N-phenylacetamide | 0.31 |
| 38 | 7-methoxy-3-(N-methyl-anilinoacetyl)coumarin | 0.03 |
| 39** | 5,7-dihydroxy-4-methyl-coumarin | 0.013 |

*BNTZ provided a relative speed of 1.0, as a further control.
**This is a control for comparison, the coumarin of which is not a sensitizer of this invention.

These results demonstrate that 5,7-dihydroxy-4-methyl-coumarin sensitizes the above-noted polymer not at all, and that the acetamide group attached to the methyl of the substituted 3-carbonyl provides a speed that is 10 times as fast as the methylanilino group in the same position.

The invention has been described in detail with particular reference to certain preferred embodiments thereof, but it will be understood that variations and modifications can be effected within the spirit and scope of the invention.

What is claimed is:

1. In a light-sensitive composition comprising, in admixture, light-sensitive material selected from the group consisting of a light-sensitive simple compound having olefinic unsaturation or an azide group (—N$_3$), or a light-sensitive polymer containing in the backbone or in pendent groups, moieties having olefinic unsaturation of an azide group (-N$_3$), and a sensitizer for said compound or polymer;

the improvement wherein said sensitizer has an absorptive maximum between about 250 and about 550 nm and the formula

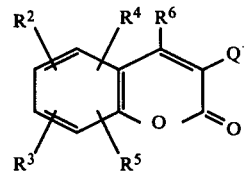

wherein Q is —CN or —Z-R$^1$; Z is carbonyl, sulfonyl, sulfinyl or arylenedicarbonyl; R$^1$ is alkenyl; alkyl having 1-12 carbon atoms; aryl of 6-10 carbon atoms; a carbocyclic group of 5-12 carbon atoms or a heteocyclic group having 5-15 nuclear carbon and hetero atoms;

R$^2$, R$^3$, R$^4$ and R$^5$ each independently is hydrogen, alkoxy having 1-6 carbon atoms, dialkylamino with each alkyl of the dialkylamino group having 1-4 carbon atoms, halogen, acyloxy, nitro, a 5- or 6-membered heterocyclic group, or a group having the formula

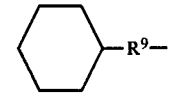

wherein R$^9$ is an alkylene having from 1-5 carbon atoms;

R$^6$ is hydrogen, alkyl having 1-4 carbon atoms, or aryl of 5-10 carbon atoms;

and wherein two or three of R$^2$ -R$^5$ and the nuclear carbon atoms to which they are attached can together form a fused ring or fused ring system, each ring being a 5- or 6- membered ring;

said sensitizer being present in an amount sufficient to appreciably increase the speed of the composition beyond that which exists without any sensitizer.

2. A light-sensitive composition as defined in claim 1 in which said heterocyclic group of R$^1$ comprises a 3-coumarinyl group having the formula:

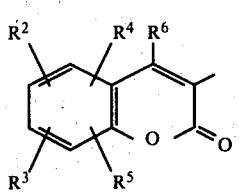

or a pyridinium group having the formula

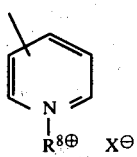

wherein $X^\ominus$ is an anion;
$R^2$, $R^3$, $R^4$, $R^5$ and $R^6$ are as defined above;
$R^8$ is alkyl having 1-4 carbon atoms; and
two or three of $R^2$–$R^5$ and the nuclear carbon atoms, to which they are attached can together form a fused ring or fused ring system, each ring being a 5- or 6-membered ring.

3. A composition as defined in claim 1, wherein Z is carbonyl.

4. A composition as defined in claim 3, wherein said sensitizer is 3,3'-carbonylbis(5,7-di-n-propoxycoumarin).

5. A composition as defined in claim 3, in which said sensitizer is 3,3'-carbonylbis(7-diethylaminocoumarin).

6. A composition as defined in claim 3, in which said sensitizer is 3-(2-benzofuroyl)-7-diethylaminocoumarin.

7. A composition as defined in claim 3, in which said sensitizer is 3-benzoyl-7-methoxycoumarin.

8. A composition as defined in claim 3, wherein said sensitizer is 3,3'-carbonylbis(5,7-diethoxycoumarin).

9. A light-sensitive composition as defined in claim 1 in which said light-sensitive material is selected from the class consisting of cinnamylideneacetate esters of poly(vinyl alcohol), cinnamic acid esters of poly(vinyl alcohol), cinnamic acid esters of cellulose, cinnamic acid esters of hydroxyalkylcellulose, cinnamoylated polystyrene, cinnamyl vinyl ketone polymers and unsaturated polyesters.

10. A composition as defined in claim 1, wherein said sensitizer is present in an amount between about 0.1 and about 20 percent by weight of the weight of said material.

11. A composition as defined in claim 1, and further including a support over which said composition is coated in dry form.

12. A light-sensitive composition comprising, a cinnamic acid ester of poly(vinyl alcohol)
and in admixture therewith, a sensitizer selected from the group consisting of
3-benzoyl-5,7-dimethoxycoumarin;
3-benzoyl-7-methoxycoumarin;
3-benzoyl-6-methoxycoumarin;
3-benzoyl-8-ethoxycoumarin;
7-methoxy-3-(p-nitrobenzoyl)coumarin;
3-benzoylcoumarin;
3-(p-nitrobenzoyl)coumarin;
3-benzoylbenzocoumarin;
3,3'-carbonylbis(7-methoxycoumarin);
3-acetyl-7-methoxycoumarin;
3-benzoyl-6-bromocoumarin;
3,3'-carbonylbiscoumarin;
3-benzoyl-7-dimethylaminocoumarin;
3,3'-carbonylbis(7-diethylaminocoumarin);
3-carboxy-7-methoxycoumarin;
3-methoxycarbonyl-6-methoxycoumarin;
3-methoxycarbonyl-7-methoxycoumarin;
3-acetylbenzocoumarin;
3-acetyl-7-methoxycoumarin;
3-(1-adamantoyl)-7-methoxycoumarin;
3-benzoyl-7-hydroxycoumarin;
3-benzoyl-6-nitrocoumarin;
3-benzoyl-7-acetoxycoumarin;
3-[3-(p-ethoxyphenyl)acryloyl]-7-methoxycoumarin;
3-benzoyl-7-diethylaminocoumarin;
7-dimethylamino-3-(4-iodobenzoyl)coumarin;
7-diethylamino-3-(4-iodobenzoyl)coumarin;
3,3'-carbonylbis(5,7-diethoxycoumarin);
3-(2-benzofuroyl)-7-(1-pyrrolidinyl)coumarin;
7-diethylamino-3-(4-dimethylaminobenzoyl)coumarin;
7-methoxy-3-(4-methoxybenzoyl)coumarin;
3-(4-nitrobenzoyl)benzocoumarin;
3-(4-ethoxycinnamoyl)-7-methoxycoumarin;
3-(4-dimethylaminocinnamoyl)coumarin;
3-(4-diphenylaminocinnamoyl)coumarin;
3-[(3-methylbenzothiazol-2-ylidene)acetyl]coumarin;
3-[(1-methylnaphtho[1,2-d]thiazol-2-ylidene)acetyl]coumarin;
3,3'-carbonylbis(6-methoxycoumarin);
3,3'-carbonylbis(7-acetoxycoumarin);
3,3'-carbonylbis(7-dimethylaminocoumarin);
3,3'-carbonylbis(5,7-di-isopropoxycoumarin);
3,3'-carbonylbis(5,7-di-n-propoxycoumarin);
3,3'-carbonylbis(5,7-di-n-butoxycoumarin);
3,3'-carbonylbis[5,7-di(2-phenylethoxy)coumarin];
3,3'-carbonylbis[5,7-di(2-chloroethoxy)coumarin];
3-cyano-6-methoxycoumarin;
3-cyano-7-methoxycoumarin;
7-methoxy-3-phenylsulfonylcoumarin;
7-methoxy-3-phenylsulfinylcoumarin;
1,4-bis(7-diethylamino-3-coumarylcarbonyl)benzene;
7-diethylamino-5',7'-dimethoxy-3,3'-carbonylbiscoumarin;
7-dimethylamino-3-thenoyl coumarin;
7-diethylamino-3-furoyl coumarin;
7-diethylamino-3-thenoyl coumarin;
3-benzoyl-7-(1-pyrrolidinyl)coumarin;
3(4-(fluorosulfonyl)benzoyl-7-methoxycoumarin;
3-(3-fluorosulfonyl)benzoyl-7-methoxycoumarin;
5,7,6'-trimethoxy-3,3'-carbonylbiscoumarin;
5,7,7'-trimethoxy-3,3'-carbonylbiscoumarin;
7-diethylamino-6'-methoxy-3,3'-carbonylbiscoumarin;
3-nicotinoyl-7-methoxycoumarin;
3-(2-benzofuroyl)-7-methoxycoumarin;
3-(7-methoxy-3-coumarinoyl)-1-methylpyridinium fluorosulfate;
3-(5,7-diethoxy-3-coumarinoyl)-1-methylpyridinium fluoroborate;
N-(7-methoxy-3-coumarinoylmethyl)pyridinium bromide;
3-(2-benzofuroyl)-7-diethylaminocoumarin;
7-(1-pyrrolidinyl)-3-thenoylcoumarin;
7-methoxy-3-(4-pyridinoyl)coumarin;
3,6-dibenzoylcoumarin;
N-(7-methoxy-3-coumarinoylmethyl)-N-phenylacetamide;
and 9-(7-diethylamino-3-coumarinoyl)-1,2,4,5-tetrahydro-3H,-6H, 10H [1]benzopyrano[9, 9a, 1- gh]quinolazine-10-one, said sensitizer being present in an amount sufficient to appreciably increase the speed of the composition beyond that which exists without any sensitizer.

13. A light-sensitive composition comprising, in admixture, a polymer containing a recurring unit having the formula

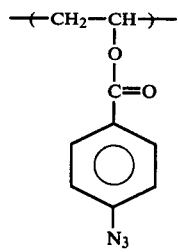

and a sensitizer selected from the group consisting of
3-benzoyl-5,7-dimethoxycoumarin;
3-benzoyl-7-methoxycoumarin;
3-benzoyl-6-methoxycoumarin;
3-benzoyl-8-ethoxycoumarin;
7-methoxy-3-(p-nitrobenzoyl)coumarin;
3-benzoylcoumarin;
3-(p-nitrobenzoyl)coumarin;
3-benzoylcoumarin;
3,3'-carbonylbis(7-methoxycoumarin);
3-acetyl-7-methoxycoumarin;
3-benzoyl-6-bromocoumarin;
3,3'-carbonylbiscoumarin;
3-benzoyl-7-dimethylaminocoumarin;
3,3'-carbonylbis(7-diethylaminocoumarin);
3-carboxycoumarin;
3-carboxy-7-methoxycoumarin;
3-methoxycarbonyl-6-methoxycoumarin;
3-ethoxycarbonyl-6-methoxycoumarin;
3-ethoxycarbonyl-7-methoxycoumarin;
3-methoxycarbonyl-7-methoxycoumarin;
3-acetylbenzocoumarin;
3-acetyl-7-methoxycoumarin;
3-(1-adamantoyl)-7-methoxycoumarin;
3-benzoyl-7-hydroxycoumarin;
3-benzoyl-6-nitrocoumarin;
3-benzoyl-7-acetoxycoumarin;
3-benzoyl-7-diethylaminocoumarin;
7-dimethylamino-3-(4-iodobenzoyl)coumarin;
7-diethylamino-3-(4-iodobenzoyl)coumarin;
3,3'-carbonylbis(5,7-diethoxycoumarin);
3-(2-benzofuroyl)-7-(1-pyrrolidinyl)coumarin;
7-diethylamino-3-(4-dimethylaminobenzoyl)coumarin;
7-methoxy-3-(4-methoxybenzoyl)coumarin;
3-(4-nitrobenzoyl)benzocoumarin;
3-(4-ethoxycinnamoyl)-7-methoxycoumarin;
3-(4-dimethylaminocinnamoyl)coumarin;
3-(4-diphenylaminocinnamoyl)coumarin;
3-[(3-methylbenzothiazol-2-ylidene)acetyl]coumarin;
3-[(1-methylnaphtho[1,2-d]thiazol-2ylidene)acetyl]coumarin;
3,3'-carbonylbis(6-methoxycoumarin);
3,3'-carbonylbis(7-acetoxycoumarin);
3,3'-carbonylbis(7-dimethylaminocoumarin);
3-[3-(p-ethoxyphenyl)acryoyl]-7-methoxycoumarin;
3,3'-carbonylbis(5,7-di-isopropoxycoumarin);
3,3'-carbonylbis(5,7-di-n-propoxycoumarin);
3,3'-carbonylbis(5,7-di-n-butoxycoumarin);
3,3'-carbonylbis[5,7-di(2-phenylethoxy)coumarin];
3,3'-carbonylbis[5,7-di(2-chloroethoxy)coumarin];
3-cyano-6-methoxycoumarin;
3-cyano-7-methoxycoumarin;
7-methoxy-3-phenylsulfonylcoumarin;
7-methoxy-3-phenylsulfinylcoumarin;
1,4-bis(7-diethylamino-3-coumarylcarbonyl)benzene;
7-diethylamino-5', 7'-dimethoxy-3,3'-carbonylbiscoumarin;
7-dimethylamino-3-theonyl coumarin;
7-diethylamino-3-furoyl coumarin;
7-diethylamino-3-theonyl coumarin;
3-benzoyl-7-(1-pyrrolidinyl)coumarin;
3-(4-fluorosulfonyl)benzoyl-7-methoxycoumarin;
3-(3-fluorosulfonyl)benzoyl-7-methoxycoumarin;
5,7,6'-trimethoxy-3,3'-carbonylbiscoumarin;
5,7,7'-trimethoxy-3,3'-carbonylbiscoumarin;
7-diethylamino-6'-methoxy-3,3'-carbonylbiscoumarin;
3-nicotinoyl-7-methoxycoumarin;
3-(2-benzofuroyl)-7-methoxycoumarin;
3-(7-methoxy-3-coumarinoyl)-1-methylpyridinium fluorosulfate;
3-(5,7-diethoxy-3-coumarinoyl)-1-methylpyridinium fluorborate;
N-(7-methoxy-3-coumarinoylmethyl)pyridinium bromide;
3-(2-benzofuroyl)-7-diethylaminocoumarin;
7-(1-pyrrolidinyl)-3-thenoylcoumarin;
7-methoxy-3-(4-pyridinoyl)coumarin;
3,6-dibenzoylcoumarin;
N-(7-methoxy-3-coumarinoylmethyl)-N-phenylacetamide;
and 9-(7-diethylamino-3-coumarinoyl)-1,2,4,5-tetrahydro-3H, 6H, 10H [1]benzopyrano[9, 9a, 1-gh]quinolazine-10-one.

14. A composition as defined in claim 39, wherein said sensitizer is 5,7,7'-trimethoxy-3,3-carbonylbiscoumarin.

15. In a light-sensitive composition comprising a light-sensitive polymer containing
a recurring unit with the structure

wherein U is a recurring unit of the main chain, Z' is selected from the group consisting of alkylene containing 1-5 carbon atoms, carbonyl, aryleneoxy and arylene containing 6-10 carbon atoms, an ester, and an ether; and p is 1 or 2, and a sensitizer for said polymer;
the improvement wherein said sensitizer has an absorptive maximum between about 250 and about 550 nm and the formula

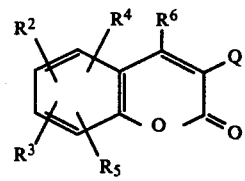

wherein Q is –CN or —Z-R$^1$; Z is carbonyl, sulfonyl, sulfinyl or arylenedicarbonyl; R$^1$ is alkenyl; alkyl having 1-12 carbon atoms; aryl of 6-10 carbon atoms; a carbocyclic group of 5–12 carbon atoms; or a heterocyclic group having 5–15 nuclear carbon and hetero atoms;

R², R³, R⁴ and R⁵ each independently is hydrogen, alkoxy having 1–6 carbon atoms, dialkylamino with each alkyl of the dialkylamino group having 1–4 carbon atoms, halogen, acyloxy, nitro, a 5- or 6-membered heterocyclic group, or a group having the formula $$\langle\bigcirc\rangle\text{—}R^9\text{—}$$

wherein R⁹ is an alkylene having from 1–5 carbon atoms;

R⁶ is hydrogen, alkyl having 1–4 carbon atoms, aryl of 6–10 carbon atoms;

and wherein two or three of R² - R⁵ and the nuclear carbon atoms to which they are attached can together form a fused ring or fused ring system, each ring being a 5- or 6-membered ring; and said sensitizer being present in an amount sufficient to appreciably increase the speed of the composition beyond that which exists without any sensitizer.

16. In a light-sensitive composition comprising, in admixture, a light-sensitive material selected from the group consisting of a light-sensitive simple compound having olefinic unsaturation or an azide group (-N₃), or a light-sensitive polymer containing in the backbone or in pendent groups, moieties having olefinic unsaturation or an azide group (-N₃);

the improvement wherein said sensitizer has an absorptive maximum between about 250 and about 550 nm and the formula $$\begin{array}{c}R^{10}\quad R^6\\ \langle\bigcirc\rangle\text{—}Q\\ R^{11}\quad O\quad O\end{array}$$

wherein Q is —CN or —Z-R¹; Z is carbonyl, sulfonyl, sulfinyl or arylenedicarbonyl; R¹ is alkenyl; alkyl having 1–12 carbon atoms; aryl of 6–10 carbon atoms; a carbocyclic group of 5–12 carbon atoms or a heterocyclic group having 5–15 nuclear carbon and hetero atoms;

R⁶ is hydrogen, alkyl having 1–4 carbon atoms, or aryl of 6–10 carbon atoms;

and at least one of R¹⁰ and R¹¹ is alkylthio having from 1–10 carbon atoms or arylthio having from 6–10 carbon atoms, the other of R¹⁰ and R¹¹ being the same or selected from the group consisting of hydrogen, alkoxy having 1–6 carbon atoms, dialkylamino with each alkyl of the dialkylamino group having 1–4 carbon atoms, halogen, acyloxy, nitro, a 5- or 6-membered heterocyclic group, or a group having the formula $$\langle\bigcirc\rangle\text{—}R^9\text{—}$$

wherein R⁹ is an alkylene having from 1–5 carbon atoms;

said sensitizer being present in an amount sufficient to appreciably increase the speed of the composition beyond that which exists without any sensitizer.

17. In a light-sensitive composition comprising a light-sensitive polymer containing a recurring unit with the structure $$\overset{\mid}{\underset{\mid}{U}}\text{—}(Z'\text{—}N_3)_p$$

wherein U is a recurring unit of the main chain, Z' is selected from the group consisting of alkylene containing 1–5 carbon atoms, carbonyl, aryleneoxy and arylene containing 6–10 carbon atoms, an ester, and an ether; and p is 1 or 2, and a sensitizer for said polymer;

the improvement wherein said sensitizer has an absorptive maximum between about 250 and about 550 nm and the formula $$\begin{array}{c}R^{10}\quad R^6\\ \langle\bigcirc\rangle\text{—}Q\\ R^{11}\quad O\quad O\end{array}$$

wherein Q is —CN or —Z-R¹; Z is carbonyl, sulfonyl, sulfinyl or arylenedicarbonyl; R¹ is alkenyl, alkyl having 1–12 carbon atoms; aryl of 6–10 carbon atoms; a carbocyclic group of 5–12 carbon atoms or a heterocyclic group having 5–15 nuclear carbon and hetero atoms;

R⁶ is hydrogen, alkyl having 1–4 carbon atoms, or aryl of 6–10 carbon atoms and at least one of R¹⁰ and R¹¹ is alkylthio having from 1–10 carbon atoms or arylthio having from 6–10 carbon atoms, the other of R¹⁰ and R¹¹ being the same or selected from the group consisting of hydrogen, alkoxy having 1–6 carbon atoms, dialkylamino with each alkyl of the dialkylamino group having 1–4 carbon atoms, halogen, acyloxy, nitro, a 5- or 6-membered heterocyclic group, or a group having the formula $$\langle\bigcirc\rangle\text{—}R^9\text{—}$$

wherein R⁹ is an alkylene having from 1–5 carbon atoms;

said sensitizer being present in an amount sufficient to appreciably increase the speed of the composition beyond that which exists without any sensitizer.

18. A composition as defined in claim 15, wherein Z' is phenylene and U is ethylene.

19. A composition as defined in claim 15, wherein Z' is carbonyl.

20. A composition as defined in claim 19, wherein said sensitizer is 3,3'-carbonylbis(5,7-di-n-propoxycoumarin).

21. A composition as defined in claim 19, in which said sensitizer is 3,3'-carbonylbis(7-diethylaminocoumarin).

22. A composition as defined in claim 19, in which said sensitizer is 3-(2-benzofuroyl)-7-diethylaminocoumarin.

23. A composition as defined in claim 19, in which said sensitizer is 3-benzoyl-7-methoxycoumarin.

24. A composition as defined in claim 19, wherein said sensitizer is 3,3'-carbonylbis(5,7-diethoxycoumarin).

* * * * *

UNITED STATES PATENT AND TRADEMARK OFFICE
CERTIFICATE OF CORRECTION

PATENT NO. : 4,147,552

DATED : April 3, 1979

INVENTOR(S) : Donald P Specht and Samir Y Farid

It is certified that error appears in the above-identified patent and that said Letters Patent are hereby corrected as shown below:

Column 1, line 27, "radaition" should read --radiation--. Column 2, line 50, "carbn" should read --carbon--; line 57, "highely" should read --highly--. Column 5, line 21, "or" should read --of --; line 45, "or" should read --of--. Column 6, line 43, that part of the formula reading "admantoy" should read --adamantoyl--; line 59, that part of the formula reading "methylbenzothiazl" should read --methylbenzothiazol --; line 66, that part of the formula reading "5,7di" should read --5,7-di--. Column 7, lines 37-38, that part of the formula reading "tetrahydro3H,6H,10H" should read tetrahydro-3H,6H,10H--. Column 9, last two lines, that part of the formula reading "3coumarinoylacetate" should read --3-coumarinoyl-acetate--. Column 13, line 53, that part of the formula reading "p" should read --$p^1$--. Column 19, lines 4-5, "-CH$_2$-COphenylene" should read -- -CH$_2$-, -CO-, phenylene, --. Column 20, line 50, "place" should read --plate--. Column 22, line 16, "A" (first occurrence) should read --Å--. Column 23, line 15, that part of the formula reading "α-naphthothiazoline" should read --β-naphthothiazoline--. Column 24, approximate columnar line 45, below the Example 10 table, --EXAMPLE 11-- should be inserted. Column 26, columnar line 8, "idential" should read --identical--. Column 27, line 10, that part of the formula reading "dimethylaino" should read --dimethylamino; line 42, that part of the formula reading

UNITED STATES PATENT AND TRADEMARK OFFICE
CERTIFICATE OF CORRECTION

PATENT NO. : 4,147,552

DATED : April 3, 1979

INVENTOR(S) : Donald P Specht and Samir Y Farid

It is certified that error appears in the above-identified patent and that said Letters Patent are hereby corrected as shown below:

"comethacrylic" should read --co-methacrylic--. Column 31, last line, "sensitizers" should read --sensitizes--. Column 32, line 15, before "light-sensitive", --a-- should be inserted; line 20, "of" should read --or--; lines 38-39, "heteocyclic" should read --heterocyclic--; line 51, . Column 33, line 64, "3-benzoylbenzocoumarin" should read --3-benzoylbenzo[f]coumarin--. Column 34, lines 3-5, "3-carboxy-7-.....-7-methoxycoumarin;" should be deleted; line 6, "3-acetylbenzocoumarin" should read --3-acetylbenzo[f]coumarin; line 21, that part of the formula reading "benzocoumarin" should read --benzo[f]coumarin; line 31, "3,3'-......-isopropoxycoumarin;" should be deleted; lines 34-35, "3,3'-carbonylbis[5,7-di(2-......-chloroethoxy)coumarin];" should be deleted. Column 35, line 28, "3-benzoylcoumarin" should read --3-benzoylbenzo[f]coumarin--; line 41, "3-acetylbenzocoumarin" should read --3-acetylbenzo[f]coumarin--; line 55, "3-(4-nitrobenzoyl)benzocoumarin" should read --3-(4-nitrobenzoyl)benzo[f]-coumarin. Column 36, line 25, "fluorborate" should read --fluoro-

UNITED STATES PATENT AND TRADEMARK OFFICE
CERTIFICATE OF CORRECTION

PATENT NO. : 4,147,552                                        Page 3 of 3

DATED : April 3, 1979

INVENTOR(S) : Donald P Specht and Samir Y Farid

It is certified that error appears in the above-identified patent and that said Letters Patent are hereby corrected as shown below:

borate--; line 38, "39" should read --13--. Column 37, line 4, "ach" should read --each--; line 37, after "(-N$_3$)", --and a sensitizer for said compound or polymer-- should be inserted.

Signed and Sealed this

Twenty-third Day of October 1979

[SEAL]

Attest:

RUTH C. MASON
Attesting Officer

LUTRELLE F. PARKER
Acting Commissioner of Patents and Trademarks